US011819801B2

(12) United States Patent
Wu et al.

(10) Patent No.: US 11,819,801 B2
(45) Date of Patent: *Nov. 21, 2023

(54) METHOD AND SYSTEM FOR RECOVERING AND PURIFYING A GASEOUS STERILIZING AGENT

(71) Applicant: TAIWAN ADVANCED STERILIZATION TECHNOLOGIES INC., Taichung (TW)

(72) Inventors: Peng-Chieh Wu, Taipei (TW); Enchi Lin, Taipei (TW)

(73) Assignee: TAIWAN ADVANCED STERILIZATION TECHNOLOGIES INC., Taichung (TW)

(*) Notice: Subject to any disclaimer, the term of this patent is extended or adjusted under 35 U.S.C. 154(b) by 17 days.

This patent is subject to a terminal disclaimer.

(21) Appl. No.: 17/531,832

(22) Filed: Nov. 22, 2021

(65) Prior Publication Data

US 2022/0080352 A1 Mar. 17, 2022

Related U.S. Application Data

(63) Continuation-in-part of application No. 16/358,726, filed on Mar. 20, 2019, now Pat. No. 11,207,612.

(51) Int. Cl.
*B01D 53/26* (2006.01)
*A61L 2/20* (2006.01)
(Continued)

(52) U.S. Cl.
CPC .......... *B01D 53/265* (2013.01); *B01D 5/009* (2013.01); *B01D 5/0051* (2013.01);
(Continued)

(58) Field of Classification Search
CPC .. B01D 53/002; B01D 53/265; B01D 5/0051; B01D 5/009; B01D 5/0036;
(Continued)

(56) References Cited

U.S. PATENT DOCUMENTS 5,283,035 A * 2/1994 Karthaus ................. A61L 2/206
422/31
11,207,612 B2 * 12/2021 Wu ........................ B01D 5/009
(Continued)

FOREIGN PATENT DOCUMENTS

CN 113509744 A * 10/2021 ........... B01D 53/002
WO WO-2015196955 A1 * 12/2015 ................ F17C 5/06

OTHER PUBLICATIONS

WO2015196955A1_ENG (Espacenet machine translation of Wang) (Year: 2015).*
(Continued)

*Primary Examiner* — Gabriel E Gitman
(74) *Attorney, Agent, or Firm* — SOROKER-AGMON-NORDMAN-RIBA; Sharone Godesh

(57) ABSTRACT

A method and system for recovering a sterilization agent and nitrogen from a waste gaseous mixture, comprising: pressure reducing valve for reducing pressure of waste gas from sterilization chambers to a first predefined pressure; a first condenser to receive the gaseous mixture and cool it to a temperature below boiling point and above freezing point of the water vapor at the first predefined pressure, to produce condensed water vapor; a first tank for storing the condensed water vapor; a separation pump for raising pressure of the gaseous mixture to a second predefined pressure; a second condenser to cool the gaseous mixture to a temperature below boiling point and above freezing point of the sterilization agent at the second predefined pressure, to condense the sterilization agent into liquid, and to discharge the nitrogen gas remaining in the gaseous mixture; a second tank for storing the sterilization agent; a compressor to compress the discharged nitrogen gas and increase pressure of the discharged nitrogen gas to a preset pressure value; and a third tank or storing the nitrogen gas for reuse.

28 Claims, 9 Drawing Sheets

(51) Int. Cl.
 _B01D 5/00_ (2006.01)
 _B01D 53/00_ (2006.01)

(52) U.S. Cl.
 CPC .............. _B01D 53/002_ (2013.01); _A61L 2/20_ (2013.01); _B01D 2256/10_ (2013.01); _B01D 2257/80_ (2013.01); _B01D 2258/02_ (2013.01)

(58) Field of Classification Search
 CPC .............. B01D 5/0093; B01D 2256/10; B01D 2257/70; B01D 2257/80; B01D 2257/93; B01D 2258/02; B01D 7/02; B01D 8/00; A61L 2202/11; A61L 2/206
 See application file for complete search history.

(56) References Cited

U.S. PATENT DOCUMENTS

2002/0168289 A1* 11/2002 McVey .................. A61L 2/208
 422/108
2019/0275184 A1* 9/2019 Duff ........................ A61L 2/206

OTHER PUBLICATIONS

CN113509744A_ENG (Espacenet machine translation of Shen) (Year: 2021).*

* cited by examiner

METHOD AND SYSTEM FOR RECOVERING AND PURIFYING A GASEOUS STERILIZING AGENT

FIELD OF THE DISCLOSURE

The present disclosure relates to gaseous sterilization agents, and more specifically to a method and system for recovering and purifying a gaseous sterilization agent.

BACKGROUND

Ethylene oxide (ETO) is a highly reactive organic compound whose high reactivity makes it useful in many different applications. Due to the high reactivity of ETO, ETO may be used as a surface disinfectant, or sterilizing agent. ETO as a sterilizing agent is well known for its effectiveness to sterilize objects at certain gas concentrations. The objects for sterilization are placed in a hermetically sealed chamber. ETO vapor is then pumped into the chamber to sterilize the objects.

However, due to the high reactivity, ETO gas is extremely flammable, toxic, and explosive. Even in the absence of air, ETO must be used with extreme caution in high concentrations at low pressures for sterilization purposes. Presently, high concentration ETO gas is not recyclable and may be used only once. After use, the ETO gas is then discharged to an emission control device for destruction.

There are a few current approaches for addressing the problem of emission and disposal of the ETO toxic gas, which solves one problem in exchange for creating another problem. For example, if ETO is absorbed into water, then the problem then becomes the treatment and discharge of the toxic water. If one tries to dispose of ETO by combustion means, the problem then becomes how to prevent an explosion (e.g., prevent an explosive reaction).

One method for reusing ETO gas involves the use of a low concentration mixture of ETO and an inert gas at higher process pressures. High process pressures (e.g., up to 4 atmospheres) allow an increase in the ETO gas concentration to an acceptable milligram per liter value for effective sterilization. Mixtures having ratios of ETO to inert gas of 10/90 and 20/80 are generally used. These mixtures have sufficient ETO concentrations to sterilize objects regardless of the material being sterilized under normal temperature and at above atmospheric pressure conditions. Relative non-flammability of diluted ETO and inert gas mixtures allows for the recycling of these mixtures. However, these mixtures are not as effective as higher concentrations of ETO gas for sterilization.

In addition, the concentration of ETO decreases with continual use during the sterilization process since ETO is consumed m reacting with bacteria, water vapor, alcohol and the like during the sterilization process. Furthermore, the ETO gas concentration may be reduced to an unsatisfactory concentration level to provide a consistent sterilization effect. Thus, low concentration gas mixtures require processing using higher pressure rated vessels, which are more expensive. This process further involves processing the gases at above atmospheric pressures which carries the risk of fugitive and catastrophic leakage. Consequently, in the industry today, all large ETO sterilizer chambers are designed to operate using low pressure and high concentrations of ETO gas. Existing sterilizers in use in the industry are not rated for the higher pressures that are required to recycle the low concentration ETO gas sterilant.

Thus, it is desirable to provide a system and method for recycling sterilant gas mixtures to a high concentration of ETO gas to obtain maximum sterilization effectiveness while minimizing the complexity of the process and the cost of the sterilization equipment. It is desirable to provide a system that can be retrofitted to existing sterilization facilities, by the utilization of the existing sterilization process equipment and avoiding the expenses that are associated with complete system replacement.

SUMMARY

There is thus provided, in accordance with some embodiments of the present disclosure, a system for recovering a sterilization agent from a waste gaseous mixture may include a pressure reducing valve for reducing a pressure of a waste gas from one or more sterilization chambers to a first predefined pressure. The waste gas may include a gaseous mixture of a sterilization agent, nitrogen gas, and water vapor. A first condenser may be configured to receive the gaseous mixture via the pressure reducing valve, and to cool the gaseous mixture to a temperature below a boiling point temperature and above a freezing point temperature of the water vapor at the first predefined pressure. A first tank, coupled to the first condenser, may store the condensed water vapor separated from the gaseous mixture in the first condenser. A separation pump coupled to the first tank may raise the pressure of the gaseous mixture to a second predefined pressure. A second condenser may be configured to receive the gaseous mixture from the separation pump, to cool the gaseous mixture to a temperature below a bailing point temperature and above a freezing point temperature of the sterilization agent at the second predefined pressure causing the sterilization agent to condense into a liquid, and to discharge the nitrogen gas remaining in the gaseous mixture. A second tank, coupled to the second condenser, may store the sterilization agent separated from the gaseous mixture in the second condenser.

Furthermore, in accordance with some embodiments of the present disclosure, the sterilization agent may include ethylene oxide (ETO).

Furthermore, in accordance with some embodiments of the present disclosure, the first predefined pressure may be 1 pound per square inch and the second predefined pressure is atmospheric pressure.

Furthermore, in accordance with some embodiments of the present disclosure, the boiling point temperature of the water vapor may be 20 deg C. when the pressure of the gaseous mixture is 1 psi.

Furthermore, in accordance with some embodiments of the present disclosure, boiling point temperature of the ETO may be 10 deg C. when the pressure of the gaseous mixture is atmospheric pressure.

Furthermore, in accordance with some embodiments of the present disclosure, the sterilization agent may be propylene oxide.

Furthermore, in accordance with souse embodiments of the present disclosure, the system may include a chamber evacuation pump coupled to the pressure reducing valve for pumping the waste gas into the first condenser.

Furthermore, in accordance with some embodiments of the present disclosure, the system may include an exhaust warmer and a freezer economizer for recovering cooling energy in the system.

Furthermore, in accordance with some embodiments of the present disclosure, the system may include one or more $H_2O$ freezers coupled to the first condenser and the separation pump, and wherein each of the one or more $H_2O$ freezers may freeze $H_2O$ molecules in the water vapor to a freezer surface.

Furthermore, in accordance with some embodiments of the present disclosure, at least two $H_2O$ freezers from the one or more $H_2O$ freezers may be connected in parallel coupled between the first condenser and the separation pump.

Furthermore, in accordance with some embodiments of the present disclosure, the system may include an ETO freezer coupled to the second condenser for trapping residual vapors of the sterilization agent.

Furthermore, in accordance with some embodiments of the present disclosure, the system may include a waste gas holding tank coupled to the pressure reducing valve and to the one or more sterilization chambers for collecting the waste gas from the one or more sterilization chambers.

Furthermore, in accordance with some embodiments of the present disclosure, the system may include one or more ETO pre-condensers placed in series before the second condenser, wherein each of the one or more pre-condensers may have progressively lower temperatures above the temperature of the second condenser.

There is further provided, in accordance with some embodiments of the present disclosure, a method for recovering a sterilization agent from a waste gaseous mixture that may include receiving a waste gas from a sterilization chamber. The waste gas may include a gaseous mixture of a sterilization agent, nitrogen gas, and water vapor, A pressure of the gaseous mixture may be reduced to a first predefined pressure so as to reduce a boiling point temperature of the sterilization agent to below the freezing point temperature of the water vapor in the gaseous mixture. The gaseous mixture with the pressure at the first predefined pressure may be cooled to a temperature below a boiling point temperature and above the freezing point temperature of the water vapor. Condensed water vapor may be removed from the gaseous mixture. The pressure of the gaseous mixture may be raised to a second predefined pressure greater than the first predefined pressure so as to elevate a boiling point temperature a the sterilization agent in the gaseous mixture. The gaseous mixture at the second predefined pressure may be cooled to a temperature below the boding point temperature and above a freezing point temperature of the sterilization agent causing the sterilization agent to condense into a liquid. The liquid sterilization agent may be separated from the gaseous mixture so as to recover the sterilization agent for reuse from the waste gas. The nitrogen gas remaining in the gaseous mixture may be discharged.

Furthermore, in accordance with some embodiments of the present disclosure, the sterilization agent may include ethylene oxide (ETO).

Furthermore, in accordance with some embodiments of the present disclosure, the first predefined pressure may be 1 pound per square inch (psi) and the second predefined pressure may be atmospheric pressure.

Furthermore, in accordance with some embodiments of the present disclosure, the boiling point temperature of the water vapor may be 20 deg C. when the pressure of the gaseous mixture is 1 psi.

Furthermore, in accordance with some embodiments of the present disclosure, the boiling point temperature of the ETO may be 10 deg C. when the pressure of the gaseous mixture is atmospheric pressure.

Furthermore, in accordance with some embodiments of the present disclosure, the sterilization agent may be propylene oxide.

Furthermore, in accordance with some embodiments of the present disclosure, discharging the nitrogen gas may include discharging the nitrogen gas to the atmosphere or collecting the discharged nitrogen gas for reuse.

Furthermore, in accordance with some embodiments of the present disclosure, the method may include recovering cooling energy in the system by using an exhaust warmer and a freezer economizer.

Furthermore, in accordance with some embodiments of the present disclosure, the method may include freezing $H_2O$ molecules in the water vapor to a freezer surface of one or more $H_2O$ freezers.

Furthermore, in accordance with some embodiments of the present disclosure, at least two $H_2O$ freezers from the one or more $H_2O$ freezers may be connected in parallel, and the method may include defrosting at least one of the $H_2O$ freezers from the at least two parallel $H_2O$ freezers.

Furthermore, in accordance with some embodiments of the present disclosure, the method may include trapping residual vapors of the sterilization agent using one or more ETO freezers coupled to the second condenser.

Furthermore, in accordance with some embodiments of the present disclosure, at least two ETO freezers from the one or more $H_2O$ freezers may be connected in parallel, and the method may include defrosting at least one of the ETO freezers from the at least two parallel ETO freezers.

Furthermore, in accordance with some embodiments of the present disclosure, the method may include collecting the waste gas from the one or more sterilization chambers in a waste gas holding tank.

Furthermore, in accordance with some embodiments of the present disclosure, the method may include setting the temperatures of each of one or more ETO pre-condensers placed in series before the second condenser to progressively lower temperatures above the temperature of the second condenser.

There is further provided, in accordance with some embodiments of the present disclosure, a system for recovering a sterilization agent and nitrogen from a waste gaseous mixture that may include a pressure reducing valve for reducing a pressure of a waste gas from one or more sterilization chambers to a first predefined pressure, the waste gas comprising a gaseous mixture of a sterilization agent, nitrogen gas, and water vapor;

a first condenser configured to receive the gaseous mixture via the pressure reducing valve, and to cool the gaseous mixture to a temperature below a boiling point temperature and above a freezing point temperature of the water vapor at the first predefined pressure to produce condensed water vapor;

a first tank, coupled to the first condenser, for storing the condensed water vapor separated from the gaseous mixture in the first condenser;

a separation pump coupled to the first condenser for raising the pressure of the gaseous mixture to a second predefined pressure;

a second condenser, configured to receive the gaseous mixture from the separation pump, to cool the gaseous mixture to a temperature below a boiling point temperature and above a freezing point temperature of the sterilization agent at the second predefined pressure causing the sterilization agent to condense into a liquid, and to discharge the nitrogen gas remaining in the gaseous mixture;

a second tank, coupled to the second condenser, for storing the sterilization agent separated from the gaseous mixture in the second condenser;

a compressor, coupled to the second condenser, configured to compress the discharged nitrogen gas and to increase pressure of the discharged nitrogen gas to a preset pressure value; and a third tank, coupled to the compressor, for storing the increased pressure nitrogen gas for reuse.

Furthermore, in accordance with some embodiments of the present disclosure, the sterilization agent may comprise ethylene oxide (ETO).

Furthermore, in accordance with some embodiments of the present disclosure, the first predefined pressure may be 1 pound per square inch and the second predefined pressure may be atmospheric pressure.

Furthermore, in accordance with some embodiments of the present disclosure, the boiling point temperature of water may be 20 deg C. when the pressure of the gaseous mixture is 1 psi.

Furthermore, in accordance with some embodiments of the present disclosure, the boiling point temperature of the ETO may be 10 deg C. when the pressure of the gaseous mixture is atmospheric pressure.

Furthermore, in accordance with some embodiments of the present disclosure, the sterilization agent may be propylene oxide.

Furthermore, in accordance with some embodiments of the present disclosure, the system may further comprise a chamber evacuation pump coupled to the pressure reducing valve for pumping the waste gas into the first condenser.

Furthermore, in accordance with some embodiments of the present disclosure, the system may further comprise an exhaust warmer and a freezer economizer for recovering cooling energy in the system.

Furthermore, in accordance with some embodiments of the present disclosure, the system may further comprise one or more $H_2O$ freezers coupled to the first condenser and the separation pump, and each of the one or more $H_2O$ freezers freezes $H_2O$ molecules in the water vapor to a freezer surface.

Furthermore, in accordance with some embodiments of the present disclosure, at least two $H_2O$ freezers from the one or more $H_2O$ freezers may be connected in parallel, coupled between the first condenser and the separation pump.

Furthermore, in accordance with some embodiments of the present disclosure, the system may further comprise one or more ETO freezers coupled to the second condenser for trapping residual vapors of the sterilization agent.

Furthermore, in accordance with some embodiments of the present disclosure, at least two ETO freezers from the one or more ETO freezers may be connected in parallel.

Furthermore, in accordance with some embodiments of the present disclosure, the system may further comprise a waste gas holding tank coupled to the pressure reducing valve and to the one or more sterilization chambers for collecting the waste gas from the one or more sterilization chambers.

Furthermore, m accordance with some embodiments of the present disclosure, the system may further comprise one or more ETO pre-condensers placed in series before the second condenser, and each of the one or more pre-condensers have progressively lower temperatures above the temperature of the second condenser.

Furthermore, in accordance with some embodiments of the present disclosure, the system may further comprise a chamber nitrogen charging, valve configured to allow stored nitrogen gas to be used or re-used in the one or more sterilization chambers.

Furthermore, in accordance with some embodiments of the present disclosure, the system may further comprise a pressure relief valve configured to exhaust excessive nitrogen gas when pressure inside the third tank exceeds the preset pressure value, and a tank charging valve configured to add fresh nitrogen to the third tank when pressure inside the third tank decreases below the preset pressure value.

There is further provided, in accordance with some embodiments of the present disclosure, a method for recovering a sterilization agent and nitrogen from a waste gaseous mixture that may include receiving a waste, gas from a sterilization chamber, the waste gas comprising a gaseous mixture of a sterilization agent, nitrogen gas, and water vapor;

reducing a pressure of the gaseous mixture to a first predefined pressure so as to reduce a boiling point temperature of the sterilization agent to below a freezing point temperature of the water vapor in the gaseous mixture;

cooling the gaseous mixture at the first predefined pressure, by a first condenser, to a temperature below a boiling point temperature and above the freezing point temperature of the water vapor, and removing condensed water vapor from the gaseous mixture;

raising the pressure of the gaseous mixture by a separation pump to a second predefined pressure greater than the first predefined pressure so as to elevate a boiling point temperature of the sterilization agent in the gaseous mixture, said separation pump being coupled to the first condenser;

cooling the gaseous mixture at the second predefined pressure, by a second condenser, to a temperature below the boiling point temperature and above a freezing point temperature of the sterilization agent causing the sterilization agent to condense into a liquid;

separating the liquid sterilization agent from the gaseous mixture so as to recover the sterilization agent for reuse from the waste gas;

discharging the nitrogen gas remaining in the gaseous mixture to a nitrogen gas compressor;

compressing the nitrogen gas, by the nitrogen gas compressor, to increase the nitrogen as pressure to a preset pressure value; and storing the increased pressure nitrogen gas at the preset pressure value, for reuse.

Furthermore, in accordance with some embodiments of the present disclosure, the sterilization agent mat comprise ethylene oxide (ETO).

Furthermore, in accordance with some embodiments of the present disclosure, the first predefined pressure may be 1 pound per square inch (psi) and the second predefined pressure may be atmospheric pressure.

Furthermore, in accordance with some embodiments of the present disclosure, the boiling point temperature of water may be 20 deg C. when the pressure of the gaseous mixture is 1 psi.

Furthermore, in accordance with some embodiments of the present disclosure, the boiling point temperature of the ETO may be 10 deg C. when the pressure of the gaseous mixture is atmospheric pressure.

Furthermore, in accordance with some embodiments of the present disclosure, the sterilization agent may be propylene oxide.

Furthermore, in accordance with some embodiments of the present disclosure, the method may further comprise recovering cooling energy in the system by using an exhaust warmer and a freezer economizer.

Furthermore, in accordance with some embodiments of the present disclosure, the method may further comprise freezing $H_2O$ molecules in the water vapor to a freezer surface of one or more $H_2O$ freezers.

Furthermore in accordance with some embodiments of the present disclosure, at least two $H_2O$ freezers from the one or more $H_2O$ freezers may be connected in parallel, and the method may further comprise defrosting at least one of the $H_2O$ freezers from the at least two parallel H2O freezers.

Furthermore, in accordance with some embodiments of the present disclosure, the method may further comprise trapping residual vapors of the sterilization agent using one or more ETO freezers coupled to the second condenser.

Furthermore, in accordance with some embodiments of the present disclosure, at least two ETO freezers from the one or more ETO freezers may be connected in parallel, and the method may further comprise defrosting at least one of the ETO freezers from the at least two parallel ETO freezers.

Furthermore, in accordance with some embodiments of the present disclosure, the method may further comprise collecting the waste gas from the sterilization chamber in a waste gas holding tank.

Furthermore, in accordance with some embodiments of the present disclosure, the method may further comprise setting the temperatures of each of one or more ETO pre-condensers placed in series before the second condenser to progressively lower temperatures above the temperature of the second condenser.

Furthermore, in accordance with some embodiments of the present disclosure, the method may further comprise exhausting excessive nitrogen gas, when pressure of the stored nitrogen gas exceeds the preset pressure value, and adding fresh nitrogen gas to the stored nitrogen gas, when pressure of the stored nitrogen gas decreases below the preset pressure value.

BRIEF DESCRIPTION OF THE DRAWINGS

In order for the embodiments of the present disclosure to be better understood and for its practical applications to be appreciated the following. Figures are provided and referenced hereafter. It should be noted that the Figures are given as examples only and in no way limit the scope of the embodiments of the present disclosure. Like components are denoted by like reference numerals.

DETAILED DESCRIPTION

Figure 1:
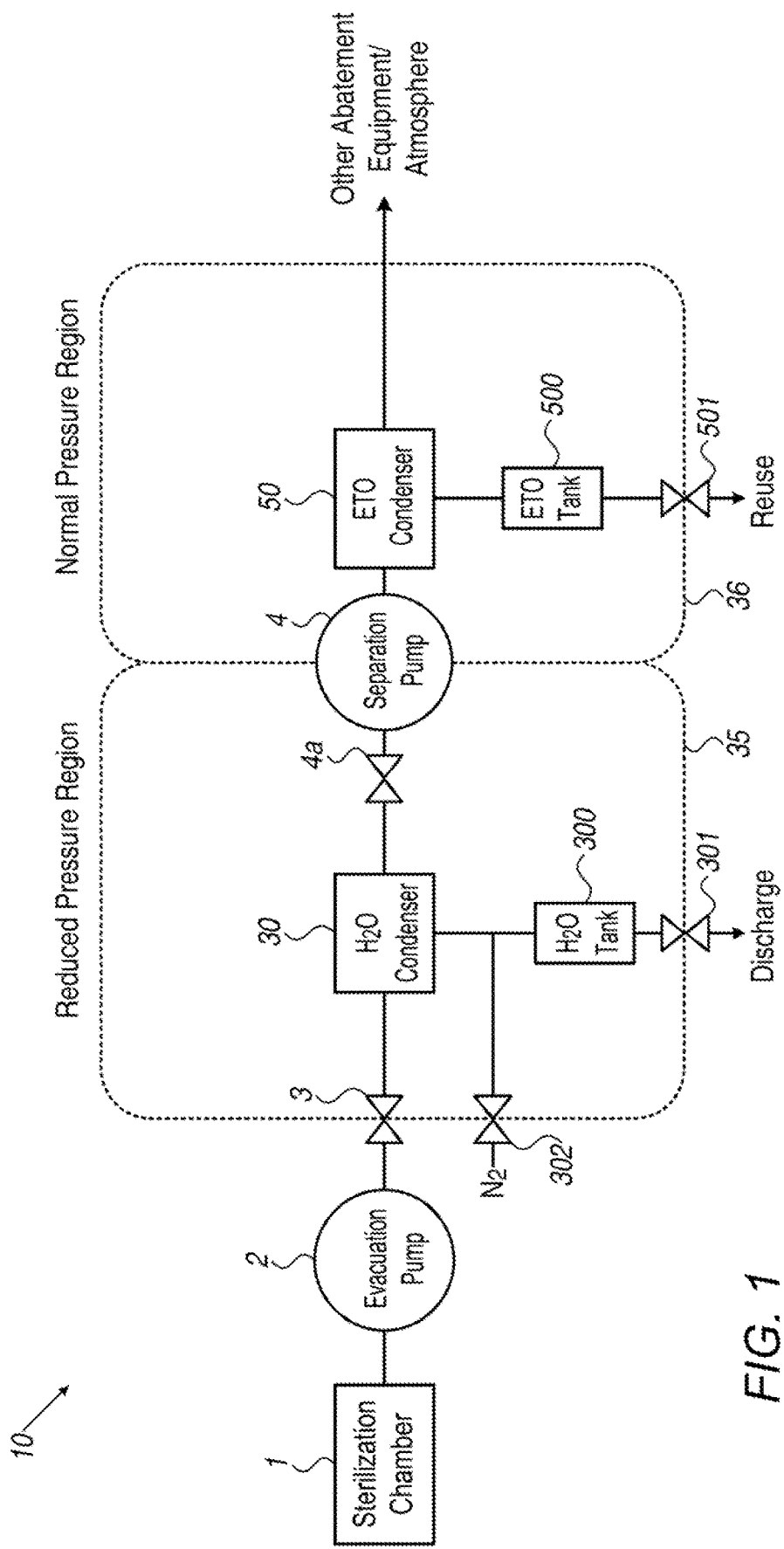
FIG. 1 schematically illustrates a block diagram of a first embodiment of a system for recovering, a sterilization agent from a waste gaseous mixture, in accordance with some embodiments of the present disclosure.

In the following detailed description, numerous specific details are set forth in order to provide a thorough understanding of the embodiments of the disclosure. However, it will be understood by those of ordinary skill in the art that the embodiments of the disclosure may be practiced without these specific details. In other instances, well-known methods, procedures, components, modules, units and/or circuits have not been described in detail so as not to obscure the embodiments of the disclosure.

Although embodiments of the disclosure are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the disclosure are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Embodiments of the present disclosure herein describe a method and a system for recovering a sterilization agent from a waste gaseous mixture. The sterilization agent as described herein may be, for example, ethylene oxide (ETO). The system may operate at pressure below and/or at atmospheric pressure and use few moving parts. The energy efficient system may be configured to recover ETO that is clean and reusable while emitting an exhaust with a level of ETO at part-per-million (ppm) levels.

After the sterilization agent is used for sterilizing items and/or objects on a closed sealed sterilization chamber, the sterilization waste gas pumped out of the sterilization chamber may include a gaseous mixture of inert nitrogen gas, the sterilization agent, such as ethylene oxide gas, and water vapor. This system leverages the differences in the vapor pressures, and the boiling and freezing points of these three gases in order to separate them. As a result, clean nitrogen gas and liquid water may be safely isolated and disposed of, while the valuable ethylene oxide gas may be recollected at high purity, suitable to be reused after appropriate quality testing.

In the embodiments taught herein, the process for recovering a sterilization agent from a waste gaseous mixture may be achieved by lowering the gas pressure to a level where the freezing point of the two components are drastically different. The ethylene oxide molecules have sufficient energy to remain in the gas phase but does not covalently bind to water molecules that are being condensed and cooled from liquid phase, and removing the water from the mixture. In some embodiments, the mixture may be further cooled such that the water molecules may be frozen into the solid phase and the solid removed.

The pressure of the dry ethylene oxide gas may be then raised to normal atmospheric pressure so as to elevate its boiling point so as to condense the ETO into a liquid, which may be removed from the nitrogen gas component of the mixture. At the end of the process, pure, uncontaminated ethylene oxide liquid may be collected, ready to be inspected and reused. Clean waste water, safe and free from ethylene oxide contamination may be collected, tested and then discharged into the environment, for example. Similarly, the separated nitrogen gas, used in the sterilization process, may be discharged into an abatement system or into the atmosphere.

This is a "clean" process where the only waste products are nitrogen gas and water. No absorption materials or metal catalysts are needed, which would need to be disposed of periodically. This is also an intrinsically safe process the operation in that the waste gas from the sterilization chamber is maintained at or below atmospheric pressure, so that there is no ethylene oxide gas leakage out from the system. Furthermore, this 'cold' process may be carried out at near normal sterilization temperatures to cryogenic temperatures minimizing the risk of catastrophic explosions by staying well below ethylene oxide's autoignition temperature.

In the context of the present disclosure, two elements that are coupled together in the systems shown herein may refer to elements that may be physically connected together by tubes and pipes, for example, that may be thermally isolated to carry refrigerants, hermetic seals for preventing leaks, pressure valves, flanges, connectors and the like. The terms used herein such as waste gas, gaseous mixture, waste gaseous mixture, gas streams are all synonymous. They refer to a waste gas that is a gaseous mixture of chemical components emitted from a sterilization chamber that is progressively processed to remove, separate and/or purify the sterilization agent from the waste gas. These terms may refer to the original waste gas with all of its chemical components exiting the sterilization chamber, or the waste gas with any or pan of its chemical components removed at any step of the process in recovering the sterilization agent.

FIG. 1 schematically illustrates a block diagram of a first embodiment of a system 10 for recovering a sterilization agent from a waste gaseous mixture, in accordance with some embodiments of the present disclosure. System 10 may include a sterilization chamber 1 coupled to a $H_2O$ condenser 30 (also known hereto as a first condenser) and an ETO condenser 50 (also known herein as a second condenser). $H_2O$ condenser 30 may be coupled to $H_2O$ tank 300 (also known herein as a first tank), and ETO condenser 50 may be coupled to ETO tank 500 (also known herein as a second tank). $H_2O$ tank 300 and ETO tank 500 may be respectively used for storing the $H_2O$ liquid and ETO during their separation processes from the gaseous mixture. The gaseous mixture of waste gas from sterilization chamber f may be pumped into $H_2O$ condenser 30 via a pressure reducing valve 3 using a chamber evacuation pump 2.

In some embodiments of the present disclosure, pressure reducing valve 3 may reduce the pressure of the gaseous mixture pumped into $H_2O$ condenser 30 to a first predefined value such as 1 psi (e.g., pound per square inch), for example, or any suitable pressure value, so as to reduce the boiling point temperature of the sterilization agent vapor component in the waste gas. The system elements operating at a reduced pressure are shown in reduced pressure region 35 (e.g., inside the dotted rectangle).

In some embodiments of the present disclosure, sterilization chamber 1 may include an enclosure with the objects and/or items to be sterilized, configured to withstand pressure variances. Sterilization chamber 1 may include inlet and/or outlet ports for removing air, injecting sterilization agent gases, and removing waste gases.

In some embodiments of the present disclosure, chamber evacuation pump 2 may include vacuum pumps of various types, capable of removing the waste gas from sterilization chamber 1.

In some embodiments of the present disclosure, system 10 may include pressure reduction valve 3 which may be a throttling valve, capable of reducing and maintaining system pressure in reduced pressure region 35.

In some embodiments of the present disclosure, $H_2O$ condenser 30 may include a shell-tube, plate or other type of heat exchanger, which may be cooled by chilled water or refrigerants. $H_2O$ condenser 30 may condense and trap water vaper and other contaminants, such as oil used by chamber evacuation pump 2. $H_2O$ condenser 30 may also allow clean ETO gas, together with other inert gases, such as nitrogen ($N_2$), to pass into ETO condenser 50.

For a pressure of 1 psi, the boiling point of water may be reduced to 20 deg C., while the boiling point of ETO is −45 deg C. $H_2O$ condenser 30 may be a heat exchanger that chills the gas mixture to about 4 deg C. to condense the water vapor and contaminants from the sterilization process of the items and/or objects in sterilization chamber 1 such as oil, polymers formed by the sterilization agent, for example, that may be mixed into the water vapor.

An $H_2O$ discharge valve 301 may be used to discharge $H_2O$ and other contaminants stored in $H_2O$ tank 300. Similarly, a vacuum release valve 302 may be used to release the vacuum inside reduced pressure region 35 so as to facilitate the discharge of material such as $N_2$ from $H_2O$ tank 300.

In some embodiments of the present disclosure, the gaseous mixture With the water vapor removed in reduced pressure region 35 may be pumped into ETO condenser 50 by a separation pump 4 via a separation valve 4A, which separates reduced pressure region 35 in system 10 from normal pressure region 36 in system 10. Separation valve 4A may allow the gaseous mixture with the water vapor removed to enter separation pump 4 which pumps the gaseous mixture into ETO condenser 50 while raising the pressure of the gaseous mixture to near atmospheric pressure.

In some embodiments of the present disclosure, separation pump 4 may include a vacuum pump capable of maintaining reduced pressures in reduced pressure region 35 (e.g., the region shown from pressure reduction valve 3 to separation pump 4). Separation pump 4 may exhaust gases against atmospheric or near atmospheric pressure in a normal pressure region 36 from separation pump 4 to other abatement equipment/atmosphere as shown in FIG. 1. Separation pump 4 may be a vacuum pump that is clean by design, namely that the vacuum pump does not introduce additional containments into the gaseous mixture. Separation pump 4 may include "dry" vacuum pumps, "oil-less" and "near-oil-less" vacuum pumps, and/or "diaphragm" vacuum pumps.

In some embodiments of the present disclosure, ETO condenser 50 may include a shell-tube, plate or other type of heat exchanger which may be cooled by coolant or refrigerant. ETO condenser 50 may condense and trap ETO vapors as well as other desirable dilutant such as $CO_2$, while allowing non-condensable dilutant such as nitrogen ($N_2$), to pass through to the other abatement equipment/atmosphere.

In some embodiments of the present disclosure, ETO condenser 50 may chill the gas mixture to a predefined temperature of about −110 deg C. (e.g., slightly higher than the ETO melting point temperature of −112 deg C.) for condensing the ETO into an ETO vapor. The ETO vapor may include $CO_2$. ETO tank 500 may be used to store the condensed ETO (and $CO_2$ mixture, if any) until reuse. An ETO discharge valve 501 may be used to discharge ETO (and $CO_2$ mixture, if any) for reuse.

The following embodiments shown in FIGS. 2-6 schematically illustrate modifications to the basic system configuration shown in FIG. 1 for improving the system energy efficiency and throughput while recovering a sterilization agent such as ETO from a waste gaseous mixture output from the sterilization chamber.

Figure 2:
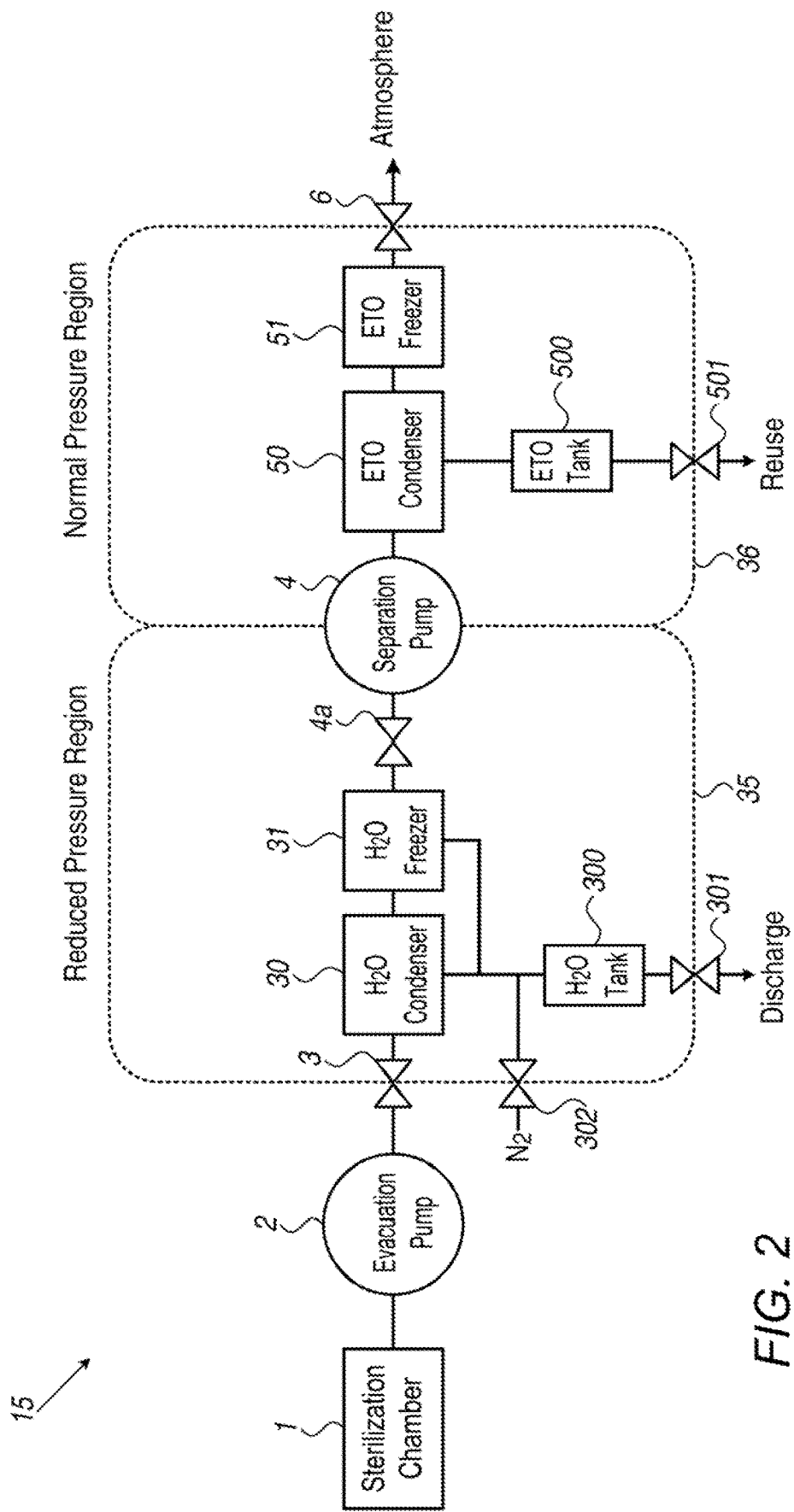
FIG. 2 schematically illustrates a block diagram of a second embodiment of a system for recovering a sterilization agent from a waste gaseous mixture, in accordance with some embodiments of the present disclosure.

FIG. 2 schematically illustrates a block diagram of a second embodiment of a system 15 for recovering a sterilization agent from a waste gaseous mixture, in accordance with some embodiments of the present disclosure. System 15 may include the same elements of system 10 as shown in FIG. 1. However, the difference between system 10 and system 15 is that system 15 may include an $H_2O$ freezer 31 after $H_2O$ condenser 30, and an ETO freezer 51 after ETO condenser 50. $H_2O$ freezer 31 and/or ETO freezer 51 are heat exchangers.

$H_2O$ Freezer 31 may be a shell-tube, plate or other type of heat exchanger, cooled by chilled water, a coolant, or a refrigerant, which may further trap residual water vapor in the gaseous mixture that may have passed through $H_2O$ condenser 30 by freezing the molecules to a surface of $H_2O$ Freezer 31. $H_2O$ Freezer 31 may allow clean ETO gas, together with other inert gases, such as nitrogen, to pass through.

Similarly, ETO Freezer 51 may be shell-tube, plate or other types, cooled by a coolant, a compressed refrigerant, or liquid gas type refrigerant, such as liquid nitrogen, for example, which may further trap residual ETO vapor and condensable dilutants such as $CO_2$ vapors, that have passed through ETO condenser 50 by freezing the molecules to a surface of ETO Freezer 51. ETO Freezer 51 may allow dean nitrogen gas to pass through an atmospheric exhaust valve 6 to the atmosphere.

Figure 3:
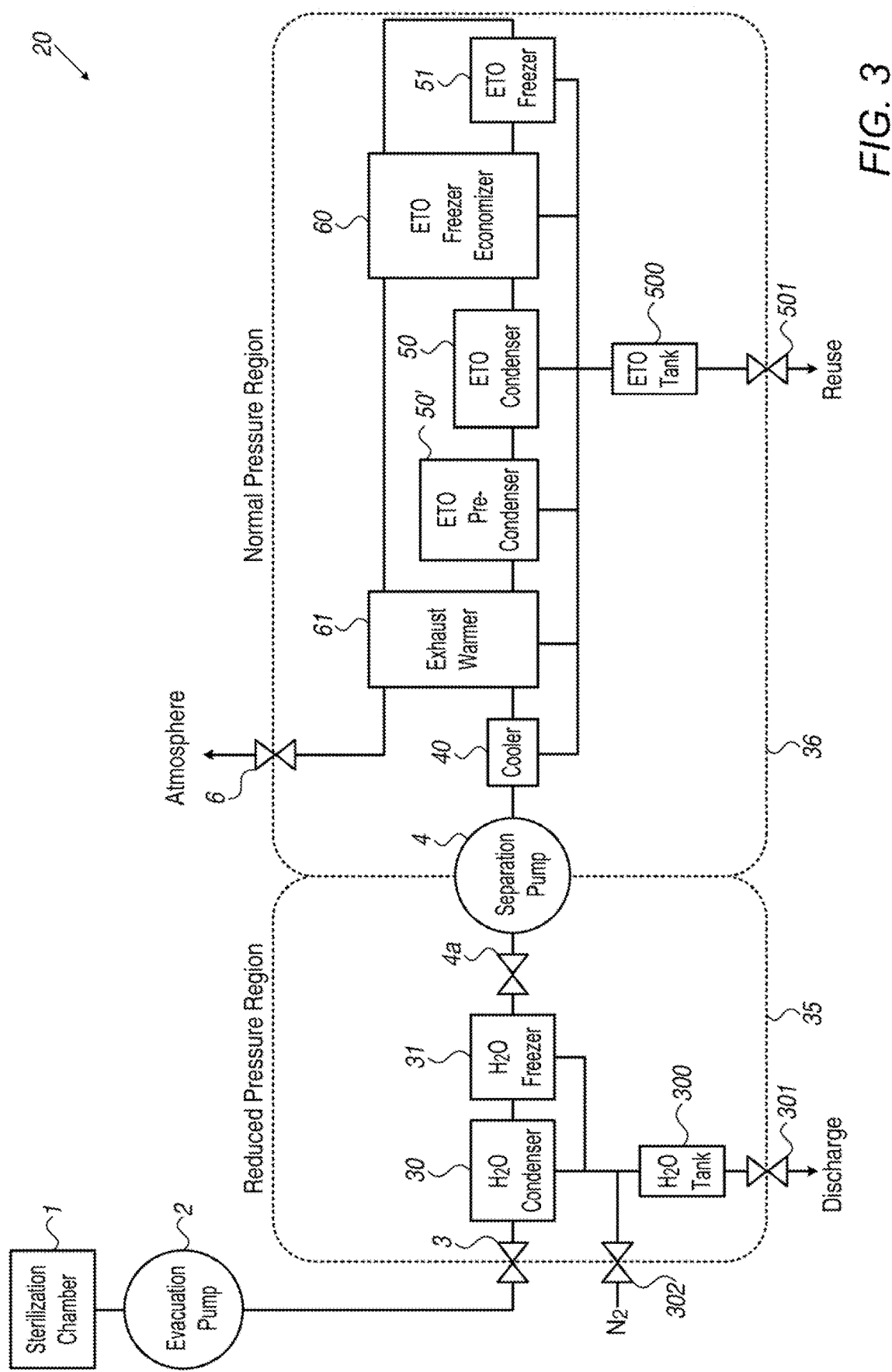
FIG. 3 schematically illustrates a block diagram of a third embodiment of a system for recovering a sterilization agent from a waste gaseous mixture, in accordance with some embodiments of the present disclosure.

FIG. 3 schematically illustrates a block diagram of a third embodiment of a system 20 for recovering a sterilization agent from a waste gaseous mixture, in accordance with some embodiments of the present disclosure. System 20 may include the same elements of system 15 as shown in FIG. 2. However, the difference between system 15 and system 20 is that between separation pump 4 and ETO condenser 50, system 20 may include an after cooler 40 coupled to separation pump 4 followed by an exhaust warmer 61 and an ETO pre-condenser 50a coupled to ETO condenser 50. Similarly, an ETO freezer economizer 60 may be coupled between ETO condenser 50 and ETO Freezer 51. Exhaust warmer 61 may also be coupled to ETO freezer economizer 60 and to atmospheric exhaust valve 6.

After cooler 40 may be a heat exchanger that may be used to cool the hot compressed gas from separation pump 4 using cold water, for example. ETO Pre-condenser 50a may include one or more heat exchangers that may be placed before and coupled to ETO condenser 50 so as to provide progressive stages of cooling the gas mixture so as to reduce the heat loading on ETO condenser 50.

ETO Freezer Economizer 60 may be a heat exchanger that pre-cools and pre-freezes the gaseous mixture entering ETO Freezer 51 using cooling energy from the exhaust gas of ETO Freezer 51.

Exhaust warmer 61 may be a heat exchanger used for pre-cooling and pre-condensing the gaseous mixture entering the ETO pre-condensers using cooling energy from the exhaust gas of ETO Freezer Economizer 60 and pre-warms the exhaust gas to near ambient temperature before venting the gas to the atmosphere via atmospheric exhaust valve 6.

Figure 4:
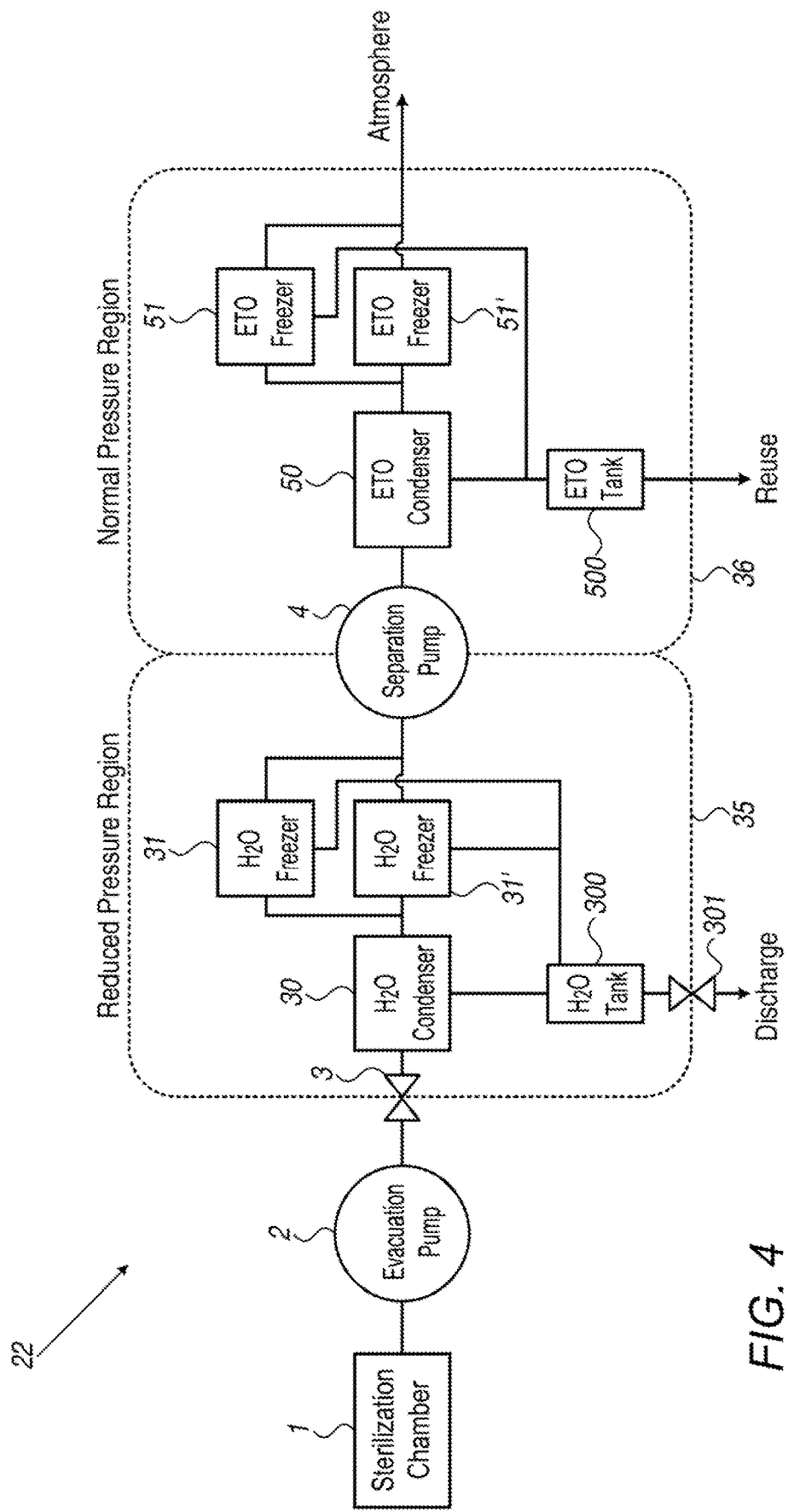
FIG. 4 schematically illustrates a block diagram of a fourth embodiment of a system for recovering a sterilization agent from a waste gaseous mixture, in accordance with some embodiments of the present disclosure.

FIG. 4 schematically illustrates a block diagram of a fourth embodiment of a system 22 for recovering a sterilization agent from a waste gaseous mixture, in accordance with some embodiments of the present disclosure. System 22 may include the same elements of system 15 as shown in FIG. 2. However, system 22 may include one or more $H_2O$ freezers and one or more ETO freezers connected in parallel. This may be shown schematically in FIG. 4 as two $H_2O$ freezers 31 and 31' and ETO Freezers 51 and 51' connected in parallel.

In some embodiments of the present disclosure, one of the $H_2O$ freezers (e.g., $H_2O$ freezer 31) may be performing the freezing operation, while the other $H_2O$ freezer (e.g., $H_2O$ freezer 31') may be thawed out or defrosted in order to prevent a build-up of solid ice on any one of the $H_2O$ freezer surfaces. Similarly, one of the ETO freezers e.g., ETO freezer 51) may be performing the freezing operation, while the other ETO freezer (e.g., ETO freezer 51') may be thawed out in order to prevent a build-up of solid ETO on any one of the $H_2O$ freezer surfaces.

In some embodiments of the present disclosure, control and/or release valves may be placed before and/or after each of the two freezers that may be placed in parallel which may be used to control which freezer may route and cool the gaseous mixture while the other freezer is defrosting or de-thawing. In this manner, the entire process does not need to be halted so as to remove solid water ice and/or solid ETO by using the ETO and/or $H_2O$ parallel freezers.

Figure 5:
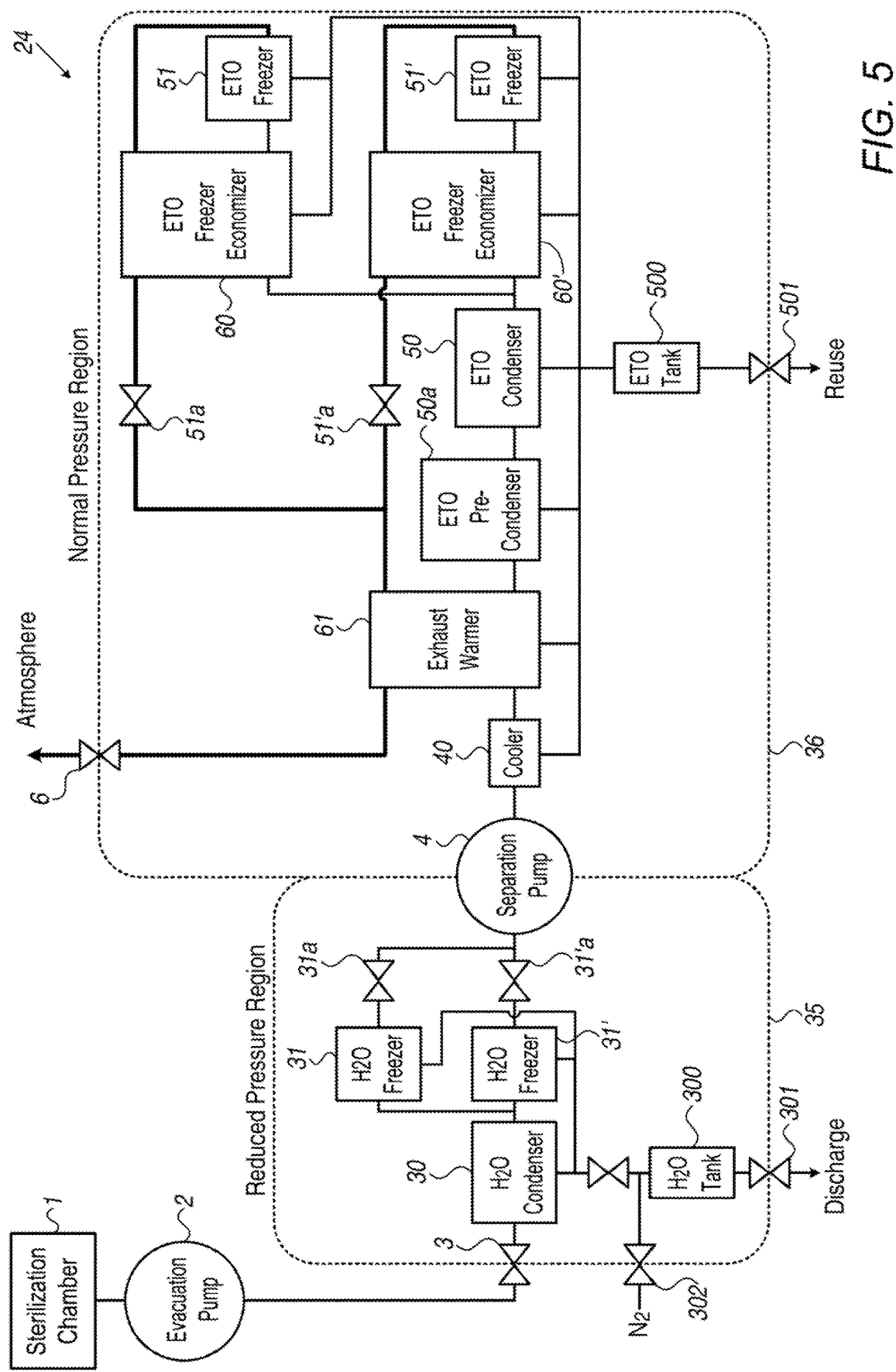
FIG. 5 schematically illustrates a block diagram of a fifth embodiment of a system for recovering a sterilization agent from a waste gaseous mixture, in accordance with some embodiments of the present disclosure.

FIG. 5 schematically illustrates a block diagram of a fifth embodiment of a system 24 for recovering a sterilization agent from a waste gaseous mixture, in accordance with some embodiments of the present disclosure. System 24 may include all of the elements of systems 20 and 24 shown in the previous FIGS. 3-4 with additional elements for further improving the energy efficiency relative to the previous figures.

The following description uses the system embodiments shown in FIG. 5 for providing a summary of the processes highlighting the different steps for recovering a sterilization agent from as Waste gaseous mixture from sterilization chamber 1 in accordance with some embodiments of the present disclosure. All or part of these steps described hereinbelow may be applicable to each of the figures described herein:

1. The objects and/or items and/or products to be sterilized may be placed in sterilization chamber 1. A gas mixture including $H_2O$ vapor, ETO with $N_2$ (and $CO_2$, if any) may be introduced into sterilization chamber 1 through conduits (not shown in FIG. 5) while pressure reducing valve 3 is in a closed position.

2. During the period of sterilizing the objects and/or items and/or products in sterilization chamber 1, $H_2O$ Condenser 30, $H_2O$ Freezers 31 and 31', After Cooler 40, ETO Pre-Condenser 50$a$, ETO Condenser 50 and/or ETO Freezers 51 and 51' may be each pre-cooled to a predefined temperature.

3. $H_2O$ Discharge Valve 301, ETO Discharge Valve 501, and Vacuum Release Valve 302 may be placed in a closed position. An $H_2O$ Tank Isolation Valve 303 may be opened while one of $H_2O$ Freezer Release Valves 31$a$ or 31'$a$ may be opened while the other remains closed. Similarly, one of ETO Freezer Release Valves 51$a$ or 51'$a$ may be opened while the other remains closed. Atmospheric Exhaust Valve 6 may be opened. Separation Pump 4 may then be activated causing the pressure inside reduced pressure region 35 to drop to lower pressure vacuum conditions. Exhaust in the system 24 may be vented through atmospheric exhaust valve 6 to the atmosphere, which keeps the pressure within the elements of normal pressure region 36 at or near atmospheric pressure.

4. After sterilization is completed, chamber evacuation pump 2 may be activated, and pressure reducing valve 3 may be opened so as to allow the waste gas from sterilizing chamber 1 to flow into $H_2O$ Condenser 30. By varying how much pressure reducing valve 3 is opened, or by varying the speed of separation pump 4, or by varying both, the vacuum inside reduced pressure region 35 may be regulated and may be maintained at a predefined pressure. In some embodiments without the use of $H_2O$ freezers, the predefined pressure ma be in the range of 10 to 0.1 psi. In other embodiments using $H_2O$ freezers, the predefined pressure may be in the range of 4 to 0.1 psi.

5. At the predefined pressure level, waste gas may flow into $H_2O$ Condenser 30, which was maintained at a predefined temperature. Upon contacting the cooling surfaces of $H_2O$ Condenser 30, $H_2O$ vapor in the stream of the waste gaseous mixture may condense into liquid form, while the ETO, $N_2$ and $CO_2$ molecules in the gaseous mixture stream of waste gas are not condensed at this predefined temperature and remain in gaseous form within the gaseous mixture. Therefore, the condensed $H_2O$ liquid may be separated from the remaining gases and collected by $H_2O$ Tank 300. Other high boiling point contaminates, such as lubricating oil mist generated by chamber evacuation pump 2, or polymers formed from the ETO, may also be separated from the waste gas stream by $H_2O$ Condenser 30. These contaminates may also be collected in $H_2O$ Tank 300.

6. The remaining stream of the gaseous mixture may exit from $H_2O$ condenser 30 into $H_2O$ freezer 31 or 31', whichever precedes the opened $H_2O$ Freezer Release Valve 31$a$ or 31$a'$, $H_2O$ Freezers 31 and 31' have been maintained at predefined temperatures, below the freezing point of $H_2O$ but above the boiling point of ETO at a predefined pressure. Upon contacting the cooling surfaces of Freezer 31 or 31$a$, the remaining water vapor in the gas stream may freeze on these cooling surfaces, further reducing the amount of water vapor in the gaseous mixture.

7. Whenever the cooling surfaces of either $H_2O$ Freezer 31 and 31' accumulate too much solid $H_2O$, and the thickness of the ice is thick enough in one of the freezers so as to inhibit proper heat transfer and efficient $H_2O$ removal from the gas stream (e.g., the gaseous mixture), then freezer release valve 31$a$ or 31$a'$ of the inefficient freezer may be closed while the other Freezer Release Valve remains opened.

8. As the gas stream is routed to the other $H_2O$ Freezer, $H_2O$ removal from the gas stream may continue inside the still-operating efficient freezer. Cooling inside the inefficient freezer with too much ice build-up may be turned off, while defrosting heaters on or near the cooling surfaces may be turned on, so as to melt the solid ice that has built up on the cooling surfaces of the inefficient Freezer back into liquid form. In other embodiments, warm fluid may be pumped into warm the cooling surfaces. This liquid, mainly water, may flow into and be further collected by $H_2O$ Tank 300 via $H_2O$ Tank isolation Valve 303. When the ice-melting and defrosting mode of the inefficiently-operating freezer has been completed, (e.g., its cooling surfaces cleared of ice built-up), the defrosting heaters may be turned off and cooling may resume to cool the Freezer hack to its predefined temperature. When the other Freezer has accumulated too much ice built-up, the same ice-removal steps can be repeated to defrost ice from its cooling surfaces. In this manner, efficient $H_2O$ removal from the gas stream may be maintained without having to stop the entire process in system 24 for ice-removal in the cooling elements.

9. Whenever $H_2O$ Tank 300 is full, $H_2O$ tank isolation valve 303 may be closed and vacuum release valve 302 may be opened to allow the pressure inside the $H_2O$ Tank 300 to return atmospheric pressure. After that, $H_2O$ Discharge Valve 301 may be opened to discharge the contents of $H_2O$ Tank 300. After discharge, valves 301 and 302 may be closed, and valve 303 may be opened. $H_2O$ Tank 300 may then continue to receive condensate from $H_2O$ Condenser 30 and $H_2O$ Freezers 31 and 31'. In this manner, $H_2O$ Tank 300 may be discharged completely while waste gas removal from Sterilization Chamber 1 may continue without interruption.

10. The remaining stream of waste gas mixture now free of $H_2O$ vapor may exit from $H_2O$ Freezers 31 and 31'. The remaining stream of waste gas mixture may include ETO vapor, $N_2$ and $CO_2$ gas, and pass through corresponding $H_2O$ Freezer Release Valve 31$a$ or 31$a'$, to separation pump 4 for compression to atmospheric or near-atmospheric pressure.

11. The compression process by separation pump 4 increases the gas stream temperature to above room temperature. The hot gas stream may then enter ETO After Cooler 40, a heat exchanger cooled by regular cooling water may be used to cool the gaseous mixture to near room temperature.

12. After being cooled by ETO After Cooler 40, the near-room temperature gas stream may enter an Exhaust Warmer 61. Exhaust Warmer 61 may be a heat exchanger that warms the final cold exhaust gas (e.g., after ETO removal) to near-room temperature before being released into the atmosphere. It may also be used to recover expensive cooling energy from that cold exhaust gas, to pre-cool the gas stream, and to pre-condense some of the ETO vapor inside the gas stream. This conserved energy may be used to cool F Pre-Condenser 50$a$.

Since the freezing point of ETO is extremely low (−112 degrees C.), ETO Condenser 50 is cooled to extremely low temperatures. In order to reduce heat load to ETO Condenser 50 (e.g., increase cooling efficiency), and to provide more effective condensing of the ETO vapor in the gaseous mixture. ETO Pre-Condenser 50*a* was placed before ETO Condenser 50 as shown in FIG. 5, which is not by way of limitation of the embodiments of the present disclosure. One or more pre-condensers may be placed in series before ETO Condenser 50. ETO Pre-Condensers may each pre-cooled to respective predefined temperatures such that each Pre-Condenser may be progressively colder (e.g., at lower temperatures) as they are positioned closer to ETO Condenser 50, with ETO Condenser 50 being, the coldest (e.g., at the lowest temperature).

As the gas stream exits from Exhaust Warmer 61 and enters ETO Pre-Condenser 50*a*, the gas stream may be pre-cooled and the ETO vapors may be pre-condensed passing through the ETO Pre-Condenser 50*a*. Similarly, if a series of ETO Pre-Condensers may be placed before ETO Condenser 50, the gas stream may be progressively cooled, with ETO vapors progressively condensed as the gas stream passes through each of ETO Pre-Condensers in series. By pre-cooling the gas stream in one single stage, or progressively pre-cooling the gas stream in multiple stages of progressively colder temperatures, the cooling system using Pre-Condensers is a more energy efficient cooling system to cool the ETO extremely low temperatures by using a series of Pre-Condensers so as to stagger the temperatures to progressively lower temperatures, yet higher than the temperature of the final ETO Condenser 50. Thus, the total energy needed to cool the gas stream was reduced, while still cooling the gas stream to the same low temperature.

13. ETO Condenser 50 may be pre-cooled and maintained at a predefined temperature as the gas stream enters ETO Condenser 50. Inside ETO Condenser 50, ETO vapor may be condensed into liquid form and was separated from the stream of the gaseous mixture. The ETO liquid may then be collected by ETO Tank 500.

Note that if $CO_2$ gas is present in the remaining gas stream from separation pump 4, it will also be frozen into solid form on the cooling surfaces of ETO Pre-Condenser 50*a* and ETO Condenser 50. $CO_2$ gas may be dissolved in the ETO liquid condensate and collected in ETO Tank 500. However, $N_2$ gas in the gas mixture will not be condensed nor frozen at the predefined temperatures of ETO Pre-Condenser 51' or ETO Condenser 50. Therefore, $N_2$ gas may be separated from the ETO condensate and $CO_2$ ice.

14. After condensable ETO vapor was removed from the gas stream by ETO Pre-Condensers 50*a* and ETO Condenser 50, the gas stream may enter ETO Freezer Economizer 60 or 60', whichever had a corresponding ETO Freezer Release Valve 51*a* or 51*a*' opened. ETO Freezer Economizer 60 and 60' may be a heat exchanger that utilizes the cooling energy from the cold exhaust of ETO Freezers 51 and 51' to pre-cool the gas stream before entering ETO Freezers 51 and 51'.

15. ETO Freezer 51 and 51' may be pre-cooled to a predefined temperature (e.g., in a range of −112 deg C. to −196 deg C.), below the freezing point of ETO and above the boiling point of $N_2$. After the gas stream enters ETO Freezers 51 and 51', the remaining ETO vapor in the gas stream may freeze onto the cooling surfaces of the ETO Freezers where the ETO may be separated from the gas stream. Consequently, ETO content in the gas stream may be reduced to a minimum level.

16. The gas stream exiting ETO Freezers 51 and 51' may include $N_2$ gas free of environmentally harmful ETO (e.g., reduced to sub-ppm levels of ETO). With all of the contaminates removed from the gaseous mixture, the remaining clean $N_2$ gas is extremely cold, and the valuable cooling energy of the $N_2$ gas may be recovered in system 24.

The cold $N_2$ gas exiting ETO Freezers 51 and 51' may be coupled into corresponding ETO Freezer Economizers 60 and 60', which are heat exchangers. The cold $N_2$ gas from ETO Freezers 51 and 51' may be used as a cooling medium that may be fed back to cool ETO Freezer Economizers 60 and 60', which may subsequently be used to cool the gas stream entering the inlets of ETO Freezers 51 and 51'.

17. Since the temperature of the $N_2$ gas is below the freezing point of ETO, ETO Freezer Economizers 60 and 60' may have solid ETO frozen onto the cooling surfaces of the Economizer. Whenever the cooling surfaces of either ETO Freezer Economizer 60 and ETO Freezer 51, or ETO Freezer Economizer 60' and ETO Freezer 51' cooling surfaces may accumulate too much solid ETO, such that the thickness of the solid ETO may inhibit proper heat transfer and efficient ETO removal from the $N_2$ gas stream, then the corresponding ETO Freezer Release Valve 51*a* or 51*a*' may be closed while the other ETO Freezer Release Valve remains open. As the gas stream may be routed to the other ETO Freezer Economizer and ETO Freezer, ETO removal from the gas stream may continue.

Cooling may be turned off in the ETO Economizer and ETO Freezer with too much solid ETO build-up, and heating applied to the cooling surfaces was turned on. The solid ETO that accumulated on the cooling surfaces of the ETO Economizer and ETO Freezer may be defrosted back into ETO liquid which may be collected by ETO Tank 500. In other embodiments, warm fluid may be pumped into warm the cooling surfaces. When ETO Economizer and ETO Freezer have been completed defrosted, heating may then be turned off and the cooling process restored, so as to cool the ETO Freezer back to its predefined temperature. Similarly, when the other ETO Freezer has accumulated too much ETO solid built-up, the same solid ETO removal steps may be repeated to clean the cooling surfaces.

18. The cold $N_2$ gas stream passing through ETO Freezer Economizer 60 or 60' may be used to transfer its cooling energy to other cooling elements in the system. For example, it may be passed though the corresponding ETO Freezer Release Valve 51*a*/51'*a*. This cold $N_2$ gas may be routed to Exhaust Warmer 61, so as to pre-cool the gas stream that was about to enter ETO Pre-Condensers 50*a*. This process may warm the clean $N_2$ gas to near room temperature as the $N_2$ gas cools the gas stream. Therefore, reducing the amount of energy needed to cool the ETO Pre-Condensers.

19. Whenever the contents of ETO Tank 500 may be discharged, ETO discharge valve 501 may be opened. Since the pressure inside ETO Tank 500 may be at or near atmospheric pressure, pure ETO stored inside ETO Tank 500 may flow out without interrupting gas removal from Sterilization Chamber 1.

20. After removal of the waste gas from Sterilization Chamber 1 is completed, Pressuring Reducing Valve 3 and H₂O Freezer Release Valves 31*a* and 31'*a* may be closed. Chamber Evacuation Pump 2 and Separation Pump 4 may be turned off.

21. In reduced pressure region 35, after ice may be removed from H₂O Freezers 31 and 31', and all condensates collected in H₂O Tank 300, valve 303 may be closed and Vacuum Release Valve 302 may be opened, so as to break the vacuum equalizing the pressure inside H₂O Tank 300 with atmospheric pressure. H₂O Discharge Valve 301 may be opened to allow the contents of H₂O Tank 300 to flow freely from the tank. The discharged contents from H₂O Tank 300 may include clean water with slight oil mists from Chamber Evacuation Pump 2 and traces of ETO polymers. This water may be easily filtered and disposed of.

22. In normal pressure region 36, after Chamber Evacuation Pump 2 and Separation Pump 4 are turned off, ETO Freezer Release Valve 51*a* and 51'*a* may be closed to prevent ETO vapor to escape into the atmosphere during ETO solid melting process in all of the cooling elements. Then, cooling of ETO Freezers 51 and 51' may be turned off and heating of the ETO Freezers 51 and 51' and ETO Freezer In other embodiments, warm fluid may be pumped into warm the cooling surfaces. Economizers 60 and 60' may be turned on. Solid ETO that collected on surfaces of ETO Freezers 51 and 51', and ETO Freezer Economizers 60 and 60' may melt back into liquid ETO, which may be collected by ETO Tank 500 for reuse.

23. After melting of solid ETO has been completed, heating of the ETO Freezers 51 and 51' and ETO Freezer Economizers 60 and 60' may be turned off. ETO Discharge Valve 501 may be opened to allow the contents of ETO Tank 500 to be discharge for re-use. Since the pressure inside normal pressure region 36 may be at or near atmospheric pressure, the contents of ETO Tank 500 may flow freely from ETO Tank 500. The contents of Tank 500 may include pure ETO, free of water and other contaminates. In some cases, the content may be a mixture of ETO and CO₂ if that was the mixture used in Sterilization Chamber 1. This mixture is also clean and free from water and other contaminates. The pure ETO, or clean ETO/CO₂ mixture, after being discharged from Tank 500, may be re-used in future processes.

The process for recovering and/or purifying a sterilization agent from a waste gas mixture as described hereinabove is not be way of limitation of the embodiments of the present disclosure. All or any steps of this process may be used in any of the FIGS. 1-6 shown herein in any suitable combination or order. The sterilization agent is not limited herein to ETO but may include other sterilization agents such as propylene oxide, for example.

Figure 6:
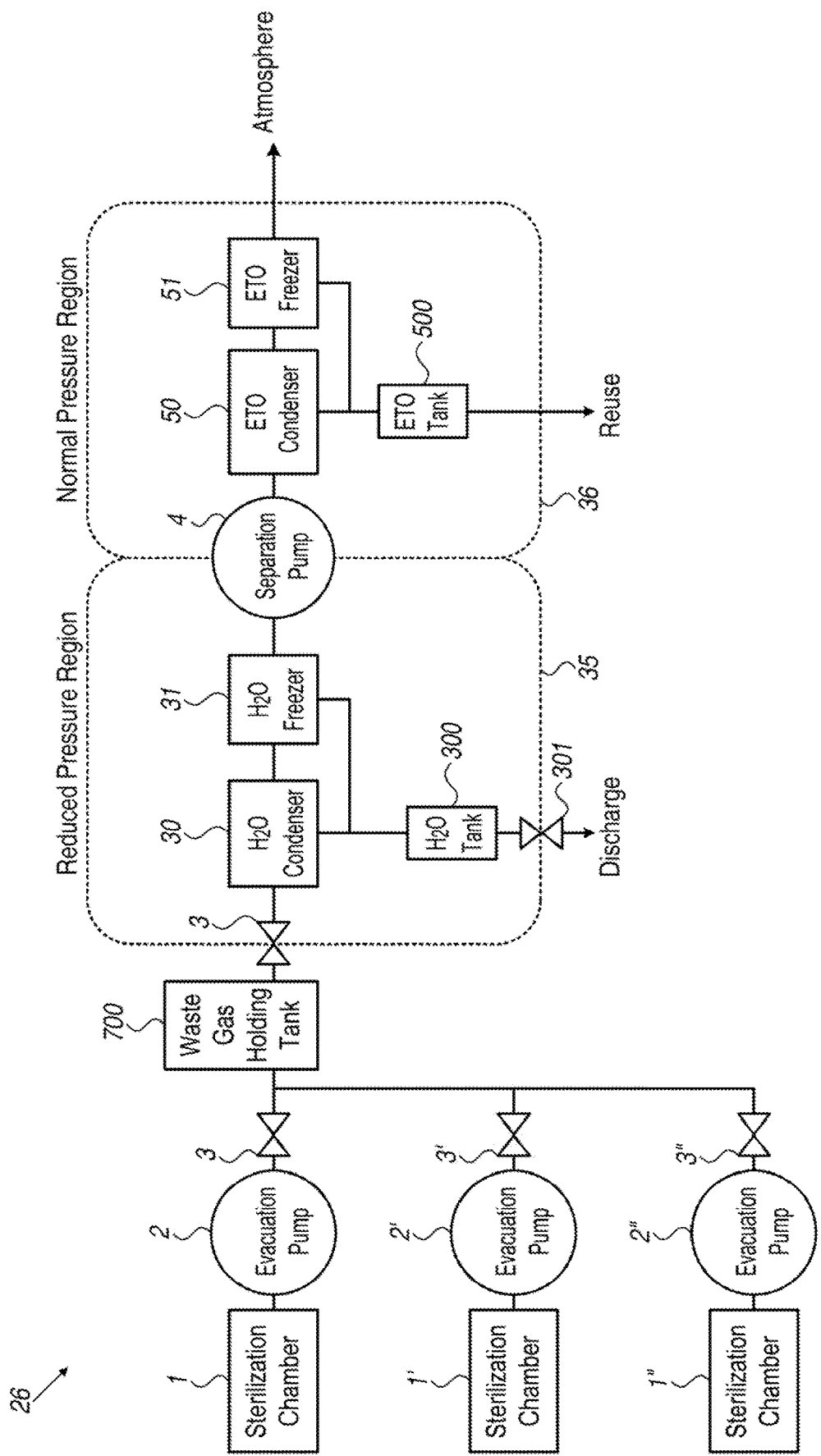
FIG. 6 schematically illustrates a block diagram of a sixth embodiment of a system for recovering a sterilization agent from a waste gaseous mixture, in accordance with some embodiments of the present disclosure.

FIG. 6 schematically illustrates a block diagram of a sixth embodiment of a system 26 for recovering a sterilization agent from a waste gaseous mixture, in accordance with some embodiments of the present disclosure. System 26 may include elements of system 15. However, the waste gaseous mixture processed by system 26 may be the waste gas from one or more sterilization chambers, denoted sterilization chamber 1, sterilization chamber 1', and sterilization chamber Each of the one or more sterilization chambers may include respective one or more evacuation pumps denoted chamber evacuation pump 2, chamber evacuation pump 2', and chamber evacuation pump 2" and one or more respective chamber waste gas exhaust valves denoted chamber waste gas exhaust valve 7, chamber waste gas exhaust valve 7', and chamber waste gas exhaust valve 7".

The waste gas from each of the one or more sterilization chambers may pass into a waste holding tank 700 and then coupled into the reduce pressure region 35 via pressure reducing valve 3 and normal pressure region 36 for recovering the ETO sterilization agent from the waste gas from the one or more sterilization chambers. Stated differently, the waste gases from the multiple sterilization chambers may be processed by a single sterilization agent recovery process system as shown in FIG. 6. Waste holding tank 700 may be of a variable volume so that pressure in the tank may be kept at atmospheric pressure, or a fixed volume type of tank.

Figure 7:
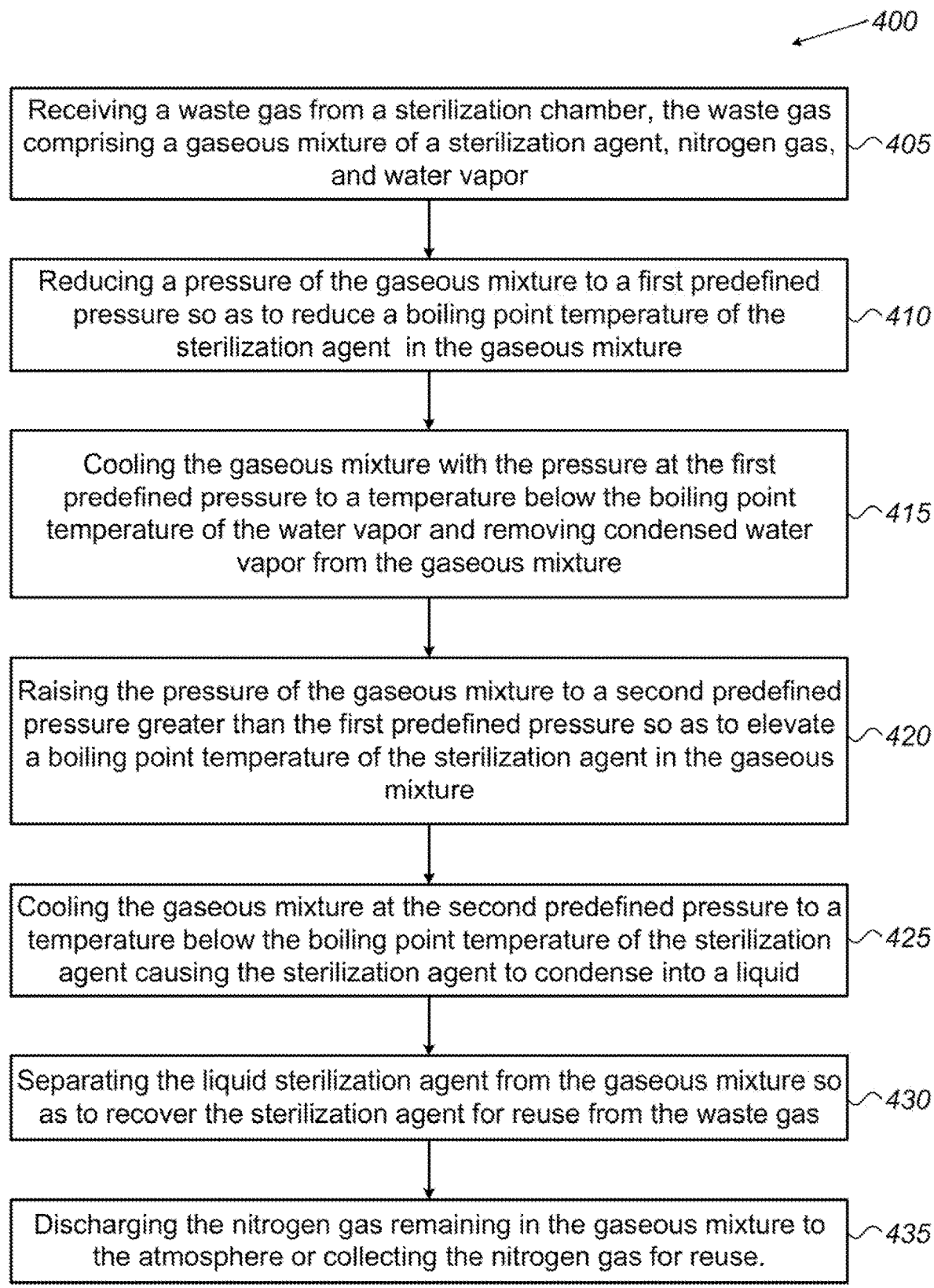
FIG. 7 is a flowchart depicting a method for recovering a sterilization agent from a waste gaseous mixture, in accordance with some embodiments of the present disclosure.

FIG. 7 is a flowchart depicting a method 400 for recovering a sterilization agent from a waste gaseous mixture, in accordance with some embodiments of the present disclosure.

Method 400 may include receiving 405 a waste gas from a sterilization chamber. The waste gas may include a gaseous mixture of a sterilization agent, nitrogen gas, and water vapor.

Method 400 may include reducing 410 a pressure of the gaseous mixture to a first predefined pressure so as to reduce a boiling point temperature of the sterilization agent to below a freezing point temperature of the water vapor in the gaseous mixture.

Method 400 may include cooling 415 the gaseous mixture with the pressure at the first predefined pressure to a temperature below a boiling point temperature and above the freezing point temperature of the water vapor, and removing condensed water vapor from the gaseous mixture.

Method 400 may include raising 420 the pressure of the gaseous mixture to a second predefined pressure greater than the first predefined pressure so as to elevate a boiling point temperature of the sterilization agent in the gaseous mixture.

Method 400 may include cooling 425 the gaseous mixture at the second predefined pressure to a temperature below the boiling point temperature and above a freezing point temperature of the sterilization agent causing the sterilization agent to condense into a liquid.

Method 400 may include separating 430 the liquid sterilization agent from the gaseous mixture so as to recover the sterilization agent for reuse from the waste gas.

Method 400 may include discharging 435 the nitrogen gas remaining in the gaseous mixture to the atmosphere or collecting the nitrogen gas for reuse.

In some embodiments of the present disclosure, a system for recovering a sterilization agent from a waste gaseous mixture may include a pressure reducing valve for reducing a pressure of a waste gas from one or more sterilization chambers to a first predefined pressure. The waste gas may include a gaseous mixture of a sterilization agent, nitrogen gas, and water vapor. A first condenser may be configured to receive the gaseous mixture via the pressure reducing valve, and to cool the gaseous mixture to a temperature below a boiling point temperature and above a freezing point temperature of the water vapor at the first predefined pressure. A first tank, coupled to the first condenser, may store the condensed water vapor separated from the gaseous mixture in the first condenser. A separation pump coupled to the first tank may raise the pressure of the gaseous mixture to a second predefined pressure. A second condenser may be configured to receive the gaseous mixture from the separation pump, to cool the gaseous mixture to a temperature below a boiling point temperature and above a freezing point temperature of the sterilization agent at the second predefined pressure causing the sterilization agent to condense into a liquid, and to discharge the nitrogen gas remaining in the gaseous mixture. A second tank, coupled to the second condenser, may store the sterilization agent separated from the gaseous mixture in the second condenser.

In some embodiments of the present disclosure, the sterilization agent may include ethylene oxide (ETO).

In some embodiments of the present disclosure, the first predefined pressure may be 1 pound per square inch and the second predefined pressure is atmospheric pressure.

In some embodiments of the present disclosure, the boiling point temperature of the water vapor may be 20 deg C. when the pressure of the gaseous mixture is 1 psi.

In some embodiments of the present disclosure, boiling point temperature of the ETO may be 10 deg C. when the pressure of the gaseous mixture is atmospheric pressure.

In some embodiments of the present disclosure, the sterilization agent may be propylene oxide.

In some embodiments of the present disclosure, the system may include a chamber evacuation pump coupled to the pressure reducing valve for pumping the waste gas into the first condenser.

In some embodiments of the present disclosure, the system may include an exhaust warmer and a freezer economizer for recovering cooling energy in the system.

In some embodiments of the present disclosure, the system may include one or more $H_2O$ freezers coupled to the first condenser and the separation pump, and wherein each of the one or more $H_2O$ freezers may freeze $H_2O$ molecules in the water vapor to a freezer surface.

In some embodiments of the present disclosure, at least two $H_2O$ freezers from the one or more $H_2O$ freezers may be connected in parallel coupled between the first condenser and the separation pump.

In some embodiments of the present disclosure, the system may include an ETO freezer coupled to the second condenser for trapping residual vapors of the sterilization agent.

In some embodiments of the present disclosure, the system may include a waste gas holding tank coupled to the pressure reducing valve and to the one or more sterilization chambers for collecting the waste gas from the one or more sterilization chambers.

In some embodiments of the present disclosure, the system may include one or more ETO pre-condensers placed in series before the second condenser, wherein each of the one or more pre-condensers may have progressively lower temperatures above the temperature of the second condenser.

In some embodiments of the present disclosure, a method for recovering a sterilization agent from a waste gaseous mixture may include receiving a waste gas from a sterilization chamber. The waste gas may include a gaseous mixture of a sterilization agent, nitrogen gas, and water vapor, A pressure of the gaseous mixture may be reduced to a first predefined pressure so as to reduce a boiling point temperature of the sterilization agent to below the freezing point temperature of the water vapor in the gaseous mixture. The gaseous mixture with the pressure at the first predefined pressure may be cooled to a temperature below a boiling point temperature and above the freezing point temperature of the water vapor. Condensed water vapor may be removed from the gaseous mixture. The pressure of the gaseous mixture may be raised to a second predefined pressure greater than the first predefined pressure so as to elevate a boiling point temperature of the sterilization agent in the gaseous mixture. The gaseous mixture at the second predefined pressure may be cooled to a temperature below the boiling point temperature and above a freezing point temperature of the sterilization agent causing the sterilization agent to condense into a liquid. The liquid sterilization agent may be separated from the gaseous mixture so as to recover the sterilization agent for reuse from the waste gas. The nitrogen gas remaining in the gaseous mixture may be discharged.

In some embodiments of the present disclosure, the sterilization agent may include ethylene oxide (ETO).

In some embodiments of the present disclosure, the first predefined pressure may be 1 pound per square inch (psi) and the second predefined pressure may be atmospheric pressure.

In some embodiments of the present disclosure, the boiling point temperature of the water vapor may be 20 deg C. when the pressing of the gaseous mixture is 1 psi.

In some embodiments of the present disclosure, the boiling point temperature of the ETO may be 10 deg C. when the pressure of the gaseous mixture is atmospheric pressure.

In some embodiments of the present disclosure, the sterilization agent may be propylene oxide (PO).

In some embodiments of the present disclosure, discharging the nitrogen gas may include discharging the nitrogen gas to the atmosphere or collecting the discharged nitrogen gas for reuse.

In some embodiments of the present disclosure, the method may include recovering cooling energy in the system by using an exhaust warmer and a freezer economizer.

In some embodiments of the present disclosure, the method may include freezing $H_2O$ molecules in the water vapor to a freezer surface of one or more $H_2O$ freezers.

In some embodiments of the present disclosure, at least two $H_2O$ freezers from the one or more $H_2O$ freezers may be connected in parallel, and the method may include defrosting at least one of the $H_2O$ freezers from the at least two parallel H2O freezers.

In some embodiments of the present disclosure, the method may include trapping residual vapors of the sterilization agent using one or more ETO freezers coupled to the second condenser In some embodiments of the present disclosure, at least two ETO freezers from the one or more $H_2O$ freezers may be connected in parallel, and the method may include defrosting at least one of the ETO freezers from the at least two parallel ETO freezers.

In some embodiments of the present disclosure, the method may include collecting the waste gas from the one or more sterilization chambers in a waste gas holding tank.

In some embodiments of the present disclosure, the method may include setting the temperatures of each of one or more ETO pre-condensers placed in series before the second condenser to progressively lower temperatures above the temperature of the second condenser.

Figure 8:
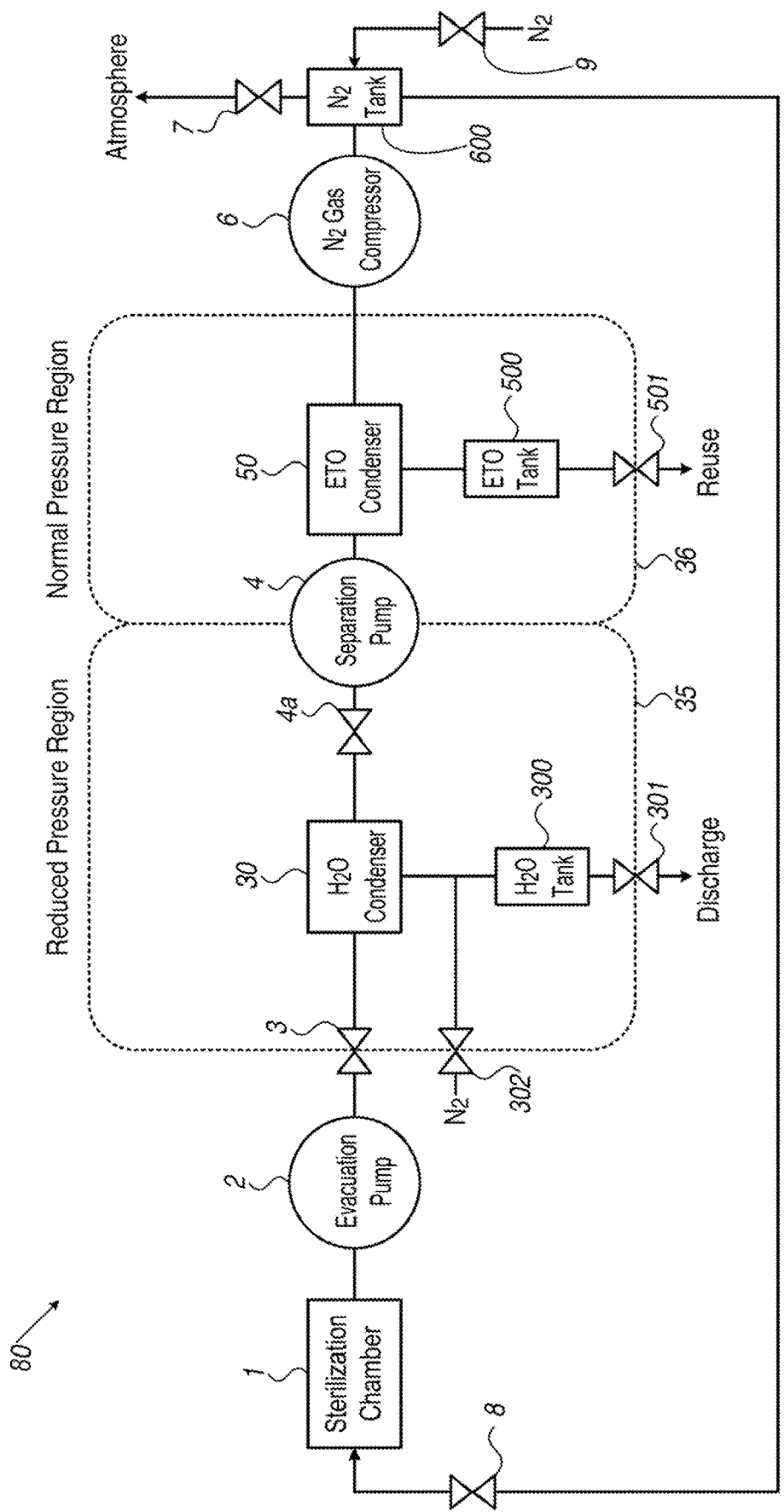
FIG. 8 schematically illustrates a block diagram of an embodiment of a system for recovering a sterilization agent and nitrogen from a waste gaseous mixture, in accordance with some embodiments of the present disclosure.

FIG. 8 schematically illustrates a block diagram of an embodiment of a system 80 for recovering a sterilization agent and nitrogen from a waste gaseous mixture, in accordance with some embodiments of the present disclosure. System 80 may comprise the same components of system 10 (FIG. 1) with the addition of components configured to enable nitrogen ($N_2$) recover and reuse.

As explained hereinabove with respect to FIG. 1, ETO condenser 50 may condense and trap ETO vapors as well as other desirable dilutant such as $CO_2$, while allowing non-condensable dilution gas such as nitrogen ($N_2$), to pass through to the other abatement equipment/atmosphere. According to some embodiments, instead of releasing the nitrogen gas to the atmosphere, the clean nitrogen gas may be collected by $N_2$ gas Compressor 6 from ETO condenser 50 or ETO freezer 51 (FIGS. 2-6). In some embodiments, N2 gas Compressor 6 may be configured to compress the clean gas and increase its gas pressure to a preset pressure value selected from a pressure range of e.g., between 30 psi to 3000 psi.

In some embodiments, system 80 may further comprise a $N_2$ Tank 600 (also known herein as a third tank), coupled to $N_2$ gas Compressor 6, which may be configured to receive the high pressurized $N_2$ gas from $N_2$ gas Compressor 6, and to store the high pressurized $N_2$ gas at its high pressure. The high pressure $N_2$ gas recovered from the waste gas may be reused, either for a sterilization process such as those disclosed throughout this disclosure or for other needs. In case the $N_2$ gas is used or re-used as part of a sterilization process, the $N_2$ gas may be exhausted from $N_2$ Tank 600 and passed into a sterilization chamber, e.g., sterilization chamber 1, via Chamber $N_2$ Charging Valve 8.

In some embodiments, system 80 may comprise a $N_2$ Pressure Relief Valve 7, which may be coupled to $N_2$ Tank 600. $N_2$ Pressure Relief Valve 7 may be configured to exhaust excessive $N_2$ gas if the pressure inside $N_2$ Tank 600 exceeds a preset pressure value, e.g., if the pressure inside $N_2$ Tank 600 exceeds 120% of a preset pressure value, which may be selected from a pressure range, e.g., between 30 psi to 3000 psi. For example, if the pressure of $N_2$ gas increases to be of a pressure value between 36 psi to 3600 psi then $N_2$ Pressure Relief Valve 7 is configured to release $N_2$ gas until the pressure within $N_2$ Tank 600 is again at the preset pressure value, e.g., at a pressure value selected from 30 psi to 3000 psi.

In some embodiments, system 80 may comprise a $N_2$ Tank Charging Valve 9, which may also be coupled to $N_2$ Tank 600, as $N_2$ Pressure Relief Valve 7 is coupled to $N_2$ Tank 600. $N_2$ Tank Charging Valve 9 may be configured to allow fresh $N_2$ gas to enter $N_2$ Tank 600 when the pressure inside $N_2$ Tank 600 reduces below a preset pressure value, e.g., when pressure of the $N_2$ gas reduces by 50% from the preset pressure value. For example, if the pressure of $N_2$ gas decreases to a pressure value between 15 psi and 1500 psi, $N_2$ Tank Charging Valve 9 is configured to allow fresh $N_2$ gas into $N_2$ Tank 600 in order to increase the $N_2$ gas pressure to the preset pressure value, e.g., to a pressure value selected from 30 psi to 3000 psi.

Figure 9:
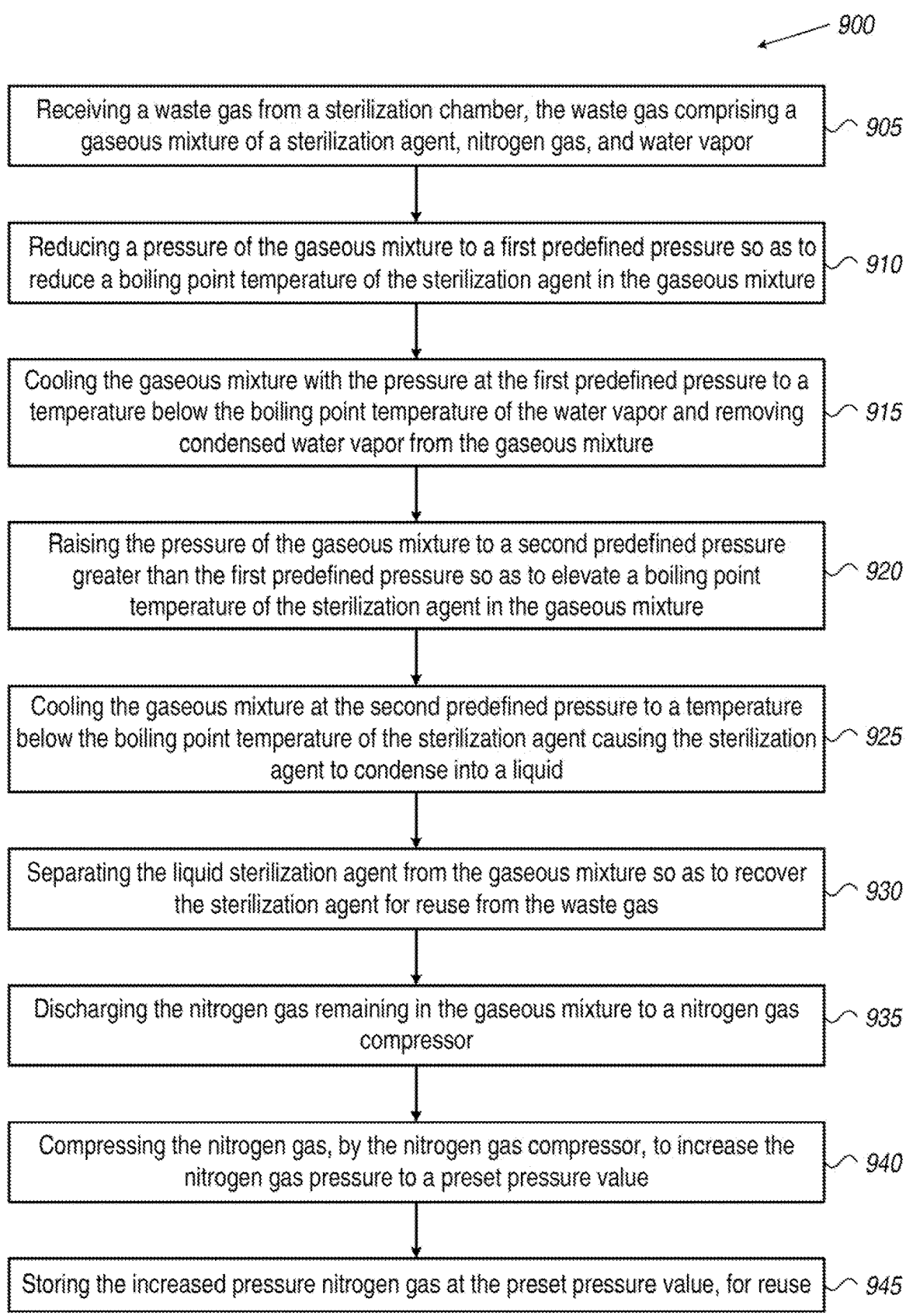
FIG. 9 is a flowchart depicting a method for recovering a sterilization agent and nitrogen from a waste gaseous mixture, in accordance with some embodiments of the present disclosure.

FIG. 9 is a flowchart depicting a method 900 for recovering a sterilization agent and nitrogen from a waste gaseous mixture, in accordance with some embodiments of the present disclosure.

Method 900 may include receiving 905 a waste gas from a sterilization chamber. The waste gas may include a gaseous mixture of a sterilization agent, nitrogen gas, and water vapor.

Method 900 may include, reducing 910 a pressure of the gaseous mixture to a first predefined pressure so as to reduce a boiling point temperature of the sterilization agent to below a freezing point temperature of the water vapor in the gaseous mixture.

Method 900 may include cooling 915 the gaseous mixture with the pressure at the first predefined pressure to a temperature below a boiling point temperature and above the freezing point temperature of the water vapor, and removing condensed water vapor from the gaseous mixture.

Method 900 may include raising 920 the pressure of the gaseous mixture to a second predefined pressure greater than the first predefined pressure so as to elevate a boiling point temperature of the sterilization agent in the gaseous mixture.

Method 900 may include cooling 925 the gaseous mixture at the second predefined pressure to a temperature below the boiling point temperature and above a freezing point temperature of the sterilization agent causing the sterilization agent to condense into a liquid.

Method 900 may include separating 930 the liquid sterilization agent from the gaseous mixture so as to recover the sterilization agent for reuse from the waste gas.

Method 900 may include discharging 935 the nitrogen gas remaining in the gaseous mixture to a nitrogen gas compressor.

Method 900 may include compressing 940 the nitrogen gas, by the nitrogen gas compressor, to increase the nitrogen gas pressure to a preset pressure value.

Method 900 may include storing 945 the increased pressure nitrogen gas at the preset pressure value, for reuse. In some embodiments, method 900 may comprise exhausting excessive nitrogen gas, when pressure of the stored nitrogen gas exceeds the preset pressure value, and adding fresh nitrogen gas to the stored nitrogen gas, when pressure of the stored nitrogen gas decreases below the preset pressure value.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Different embodiments are disclosed herein. Features of certain embodiments may be combined with features of other embodiments; thus certain embodiments may be combinations of features of multiple embodiments. The foregoing description of the embodiments of the disclosure has been presented for the purposes of illustration and description. It is not intended to be exhaustive or to limit the disclosure to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the disclosure.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the disclosure.

The invention claimed is:

1. A system for recovering a sterilization agent and nitrogen from a waste gaseous mixture, the system comprising:

a pressure reducing valve for reducing a pressure of a waste gas from one or more sterilization chambers to a first predefined pressure, the waste gas comprising a gaseous mixture of a sterilization agent, nitrogen gas, and water vapor;

a first condenser configured to receive the gaseous mixture via the pressure reducing valve, and to cool the gaseous mixture to a temperature below a boiling point temperature and above a freezing point temperature of the water vapor at the first predefined pressure to produce condensed water vapor;

a first tank, coupled to the first condenser, for storing the condensed water vapor separated from the gaseous mixture in the first condenser;

a separation pump coupled to the first condenser for raising the pressure of the gaseous mixture to a second predefined pressure;

a second condenser, configured to receive the gaseous mixture from the separation pump, to cool the gaseous mixture to a temperature below a boiling point temperature and above a freezing point temperature of the sterilization agent at the second predefined pressure causing the sterilization agent to condense into a liquid, and to discharge the nitrogen gas remaining in the gaseous mixture;

a second tank, coupled to the second condenser, for storing the sterilization agent separated from the gaseous mixture in the second condenser;

a compressor, coupled to the second condenser, configured to compress the discharged nitrogen gas and to increase a pressure of the discharged nitrogen gas to a preset pressure value; and a third tank, coupled to the compressor, for storing the increased pressure nitrogen gas for reuse; and further comprising one or more ETO pre-condensers placed in series before the second condenser, wherein each of the one or more pre-condensers has progressively lower temperatures above the temperature of the second condenser.

2. The system according to claim 1, wherein the sterilization agent comprises ethylene oxide (ETO).

3. The system according to claim 2, wherein the first predefined pressure is 1 pound per square inch and the second predefined pressure is atmospheric pressure.

4. The system according to claim 3, wherein the boiling point temperature of water is 20 deg C. when the pressure of the gaseous mixture is 1 psi.

5. The system according to claim 3, wherein the boiling point temperature of the ETO is 10 deg C. when the pressure of the gaseous mixture is atmospheric pressure.

6. The system according to claim 1, wherein the sterilization agent is propylene oxide.

7. The system according to claim 1, further comprising a chamber evacuation pump coupled to the pressure reducing valve for pumping the gaseous mixture into the first condenser.

8. The system according to claim 1, further comprising an exhaust warmer and a freezer economizer for recovering cooling energy in the system.

9. The system according to claim 1, further comprising one or more $H_2O$ freezers coupled to the first condenser and the separation pump, and wherein each of the one or more $H_2O$ freezers freezes $H_2O$ molecules in the water vapor to a freezer surface.

10. The system according to claim 9, wherein at least two $H_2O$ freezers from the one or more $H_2O$ freezers are connected in parallel, coupled between the first condenser and the separation pump.

11. The system according to claim 1, further comprising one or more ETO freezers coupled to the second condenser for trapping residual vapors of the sterilization agent.

12. The system according to claim 11, wherein at least two ETO freezers from the one or more ETO freezers are connected in parallel.

13. The system according to claim 1, further comprising a waste gas holding tank coupled to the pressure reducing valve and to the one or more sterilization chambers for collecting the waste gas from the one or more sterilization chambers.

14. The system according to claim 1, further comprising a chamber nitrogen charging valve configured to allow stored nitrogen gas to be used or re-used in the one or more sterilization chambers.

15. The system according to claim 1, further comprising a pressure relief valve configured to exhaust excessive nitrogen gas when pressure inside the third tank exceeds the preset pressure value, and a tank charging valve configured to add flesh nitrogen to the third tank when pressure inside the third tank decreases below the preset pressure value.

16. A method for recovering a sterilization agent and nitrogen from a waste gaseous mixture, the method comprising:

receiving a waste gas from a sterilization chamber, the waste gas comprising a gaseous mixture of a sterilization agent, nitrogen gas, and water vapor;

reducing a pressure of the gaseous mixture to a first predefined pressure so as to reduce a boiling point temperature of the sterilization agent to below a freezing point temperature of the water vapor in the gaseous mixture;

cooling the gaseous mixture at the first predefined pressure, by a first condenser, to a temperature below a boiling point temperature and above the freezing point temperature of the water vapor, and removing condensed water vapor from the gaseous mixture;

raising the pressure of the gaseous mixture by a separation pump to a second predefined pressure greater than the first predefined pressure so as to elevate a boiling point temperature of the sterilization agent in the gaseous mixture, said separation pump being coupled to the first condenser;

cooling the gaseous mixture at the second predefined pressure, by a second condenser, to a temperature below the boiling point temperature and above a freezing point temperature of the sterilization agent causing the sterilization agent to condense into a liquid;

separating the liquid sterilization agent from the gaseous mixture so as to recover the sterilization agent for reuse from the waste gas;

discharging the nitrogen gas remaining in the gaseous mixture to a nitrogen gas compressor;

compressing the nitrogen gas, by the nitrogen gets compressor, to increase the nitrogen gas pressure to a preset pressure value; and storing the increased pressure nitrogen gas at the preset pressure value, for reuse; and further comprising setting the temperatures of each of one or more ETO pre-condensers placed in series before the second condenser to progressively lower temperatures above the temperature of the second condenser.

17. The method according to claim 16, wherein the sterilization agent comprises ethylene oxide (ETD).

18. The method according to claim 17, wherein the first predefined pressure is 1 pound per square inch (psi) and the second predefined pressure is atmospheric pressure.

19. The method according to claim 18, wherein the boiling point temperature of water is 20 deg C. when the pressure of the gaseous mixture is 1 psi.

20. The method according to claim 18, wherein the boiling point temperature of the ETO is 10 deg C. when the pressure of the gaseous mixture is atmospheric pressure.

21. The method according to claim 17, wherein the sterilization agent is propylene oxide.

22. The method according to claim 16, further comprising recovering cooling energy in the system by using an exhaust warmer and a freezer economizer.

23. The method according to claim 17, further comprising freezing $H_2O$ molecules in the water vapor to a freezer surface of one or more $H_2O$ freezers.

24. The method according to claim 23, wherein at least two $H_2O$ freezers from the one or more $H_2O$ freezers are connected in parallel, and further comprising defrosting at least one of the $H_2O$ freezers from the at least two parallel H2O freezers.

25. The method according to claim 16, further comprising trapping residual vapors of the sterilization agent using one or more ETO freezers coupled to the second condenser.

26. The method according to claim 25, wherein at least two ETO freezers from the one or more ETO freezers are connected in parallel, and farther comprising defrosting at least one of the ETO freezers from the at least two parallel ETO freezers.

27. The method according to claim 16, further comprising collecting the waste gas from the sterilization chamber in a waste gas holding tank.

28. The method according to claim 16, further comprising exhausting excessive nitrogen gas, when pressure of the stored nitrogen gas exceeds the preset pressure value, and adding fresh nitrogen gas to the stored nitrogen gas, when pressure of the stored nitrogen gas decreases below the preset pressure value.

* * * * *